United States Patent
Lee et al.

(10) Patent No.: US 10,031,102 B2
(45) Date of Patent: Jul. 24, 2018

(54) SINGLE-WALLED CARBON NANOTUBE BIOSENSOR FOR DETECTION OF GLUCOSE, LACTATE, AND UREA

(71) Applicant: Northeastern University, Boston, MA (US)

(72) Inventors: Jin Young Lee, Seoul (KR); Ahmed Busnaina, Needham, MA (US); Hanchul Cho, Gyeonggi-do (KR); Sivasubramanian Somu, Natick, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 14/910,294

(22) PCT Filed: Aug. 5, 2014

(86) PCT No.: PCT/US2014/049815
§ 371 (c)(1),
(2) Date: Feb. 5, 2016

(87) PCT Pub. No.: WO2015/021063
PCT Pub. Date: Feb. 12, 2015

(65) Prior Publication Data
US 2016/0178567 A1 Jun. 23, 2016

Related U.S. Application Data
(60) Provisional application No. 61/862,200, filed on Aug. 5, 2013.

(51) Int. Cl.
*G01N 27/00* (2006.01)
*G01N 33/00* (2006.01)
(Continued)

(52) U.S. Cl.
CPC .......... *G01N 27/4146* (2013.01); *B82Y 15/00* (2013.01); *C12Q 1/005* (2013.01);
(Continued)

(58) Field of Classification Search
CPC .......... G01N 27/00; G01N 33/00; A61B 5/00; A61B 5/05
(Continued)

(56) References Cited

U.S. PATENT DOCUMENTS 7,955,483 B2    6/2011   Gu
2005/0061451 A1* 3/2005  Busnaina ............ B82B 1/00
                                              156/598

(Continued)

FOREIGN PATENT DOCUMENTS

WO    02/095099 A1    11/2002
WO    2008/147394 A1  12/2008

(Continued)

OTHER PUBLICATIONS

K. Besteman, et al., "Enzyme-Coated Carbon Nanotubes as Single-Molecule Biosensors", Nano Letters, (2003), vol. 3, No. 6, pp. 727-730.

(Continued)

*Primary Examiner* — Brian J. Sines
(74) *Attorney, Agent, or Firm* — Posternak Blankstein & Lund LLP

(57) ABSTRACT

A single-walled carbon nanotube-based micron scale multiplex biosensor is provided that enables the detection of glucose, lactate, and urea. The sensor is based on modification of semiconducting single-walled carbon nanotubes using a linker that non-covalently associates with the nanotubes and covalently couples to an enzyme. Reaction of a physiological substrate with the enzyme results in increased resistance of the nanotubes within the sensor. The sensor is (Continued)

suitable for use in patient monitoring, particularly in a clinical setting. Incorporation of read out electronics and an RF signal generator into the sensor device enables it to communicate to a relay station or remote receiver. Methods are also provided for fabricating the biosensor device and using the device for detection.

11 Claims, 22 Drawing Sheets

(51) Int. Cl.
    *G01N 27/414* (2006.01)
    *C12Q 1/58* (2006.01)
    *C12Q 1/00* (2006.01)
    *B82Y 15/00* (2011.01)
    *C12Q 1/26* (2006.01)
    *C12Q 1/54* (2006.01)
    *H01L 29/40* (2006.01)
    *G01N 27/12* (2006.01)

(52) U.S. Cl.
    CPC .............. *C12Q 1/006* (2013.01); *C12Q 1/26* (2013.01); *C12Q 1/54* (2013.01); *C12Q 1/58* (2013.01); *H01L 29/401* (2013.01); *G01N 27/127* (2013.01)

(58) Field of Classification Search
    USPC ..... 422/68.1, 82.01, 82.02; 436/43, 95, 108; 977/700, 742, 743, 750, 904, 953, 957, 977/958; 600/300, 347, 365
    See application file for complete search history.

(56) References Cited

U.S. PATENT DOCUMENTS

| | | | |
|---|---|---|---|
| 2005/0265914 A1* | 12/2005 | Gu ......................... | B82Y 15/00 423/445 B |
| 2009/0087622 A1* | 4/2009 | Busnaina ............ | B81C 1/00031 428/173 |
| 2010/0072062 A1* | 3/2010 | Curry ................. | A61B 5/14532 204/403.11 |
| 2012/0018301 A1 | 1/2012 | Joshi et al. | |
| 2013/0078622 A1 | 3/2013 | Collins et al. | |
| 2014/0093769 A1* | 4/2014 | Busnaina ............. | H01M 4/625 429/156 |
| 2014/0197046 A1* | 7/2014 | Busnaina ............. | G01N 27/127 205/786.5 |

FOREIGN PATENT DOCUMENTS

| | | |
|---|---|---|
| WO | 2013/036617 A1 | 3/2013 |
| WO | 2013/081684 A2 | 6/2013 |

OTHER PUBLICATIONS

G.J. Lee, et al., "Real-time Detection of Neurotransmitter using Enzyme-immobilized CNT Network Transistors in 11 Vessel Occlusion Rat Model", NSTI-Nanotech, (2008), vol. 2, pp. 646-648.

L. Cella, et al., "Single-Walled Carbon Nanotube-Based Chemiresistive Affinity Biosensors for Small Molecules: Ultrasensitive Glucose Detection", J. Am. Chem. Soc., (2010), vol. 132, pp. 5024-5026.

A. Merkoçi, et al., "New materials for electrochemical sensing VI: Carbon nanotubes", Trends in Analytical Chemistry (2005), vol. 24, No. 9, pp. 826-838.

F. Khan, et al., "Double-Hexahistidine Tag with High-Affinity Binding for Protein Immobilization, Purification, and Detection on Ni-Nitrilotriacetic Acid Surfaces", Anal. Chem., (2006), vol. 78, pp. 3072-3079.

W. Kusnezow, et al., "Solid supports for microarray immunoassays", Journal of Molecular Recognition, (2003), vol. 16, pp. 165-176.

E. Katz, et al., A non-compartmentalized glucose O2 biofuel cell by bioengineered electrode surfaces, Journal of Electroanalytical Chemistry, (1999), vol. 479, pp. 64-68.

J.Y. Lee, et al., "A novel enzyme-immobilization method for a biofuel cell", Journal of Molecular Catalysis B: Enzymatic, (2009), vol. 59, pp. 274-278.

A. Ramanavicius, et al., "Biofuel cell based on direct bioelectrocatalysts", Biosensors and Bioelectronics, (2005), vol. 20, pp. 1962-1967.

C. Tlili, et al., "Single-walled carbon nanotube chemoresistive label-free immunosensor for salivary stress biomarkers", Analyst, (2010), vol. 135, pp. 2637-2642.

M.R. Leyden, et al., "Fabrication and Characterization of Carbon Nanotube Field-Effect Transistor Biosensors", Organic Semiconductors in Sensors and Bioelectronics III, Proc. of SPIE, vol. 7779, (2010), 11 pgs.

J.P. Kim, et al., "Ultrasensitive carbon nanotube-based biosensors using antibody-binding fragments", Analytical Biochemistry, (2008), vol. 381, pp. 193-198.

V. A. Karachevtsev, et al., "Glucose Oxidase Immobilization onto Carbon Nanotube Networking", Ukranian Journal of Phy., (2013) vol. 57, No. 7, pp. 700-709.

M Holzinger, et al., "Multiple functionalization of single-walled carbon nanotubes by dip coating", Chem. Commun., (2011), vol. 47, pp. 2450-2452.

C. Garcia-Aljaro, et al., "Carbon nanotubes-based chemiresistive biosensors for detection of microorganisms", Biosensors and Bioelectronics, (2010), vol. 26, pp. 1437-1441.

B. Kim, et al., "Family-selective detection of antibiotics using antibody-functionalized carbon nanotube sensors", Sensors and Actuators B, (2012), vols. 166-167, pp. 193-199.

Besteman, Koen, et al. "Enzyme-coated nanotubes as single-molecule biosensors." Nano Letters 3.6 (2003): 727-730.†

Allen, Brett Lee, Padmakar D. Kichambare, and Alexander Star. "Carbon nanotube field-effect-transistor-based biosensors." Advanced Materials 19.11 (2007): 1439-1451 (Review article).†

\* cited by examiner
† cited by third party

SINGLE-WALLED CARBON NANOTUBE BIOSENSOR FOR DETECTION OF GLUCOSE, LACTATE, AND UREA

CROSS REFERENCE TO RELATED APPLICATIONS

This application claims the priority of U.S. Provisional Application No. 61/862,200, filed Aug. 5, 2013 and entitled "s-SWNT Biosensors for Detection of Glucose Lactate and Urea", the whole of which is hereby incorporated by reference.

BACKGROUND

There has been significant interest in using carbon-based nanomaterials as chemical sensors due to advantages such as light weight, high electrical conductivity, high electrochemical surface area, and superior sensing performance. Carbon nanotubes (CNT), including single-walled carbon nanotubes (SWNT or SWCNT), are particularly attractive due to their high electron mobility and large current carrying capacity. CNT can reduce power consumption and exhibit high temperature stability and chemical inertness, providing a stable and robust platform to detect specific analytes. Chemical sensors containing untreated CNTs utilize their intrinsic electrochemical properties, which limits the sensor selectivity and sensitivity. One approach to improving selectivity has been to functionalize CNTs either covalently or non-covalently with various materials. However, owing to their one-dimensional nanostructure, CNTs are highly sensitive to environmental factors such as humidity and temperature, which can restrict their use depending on the season, region, and weather. Thus, there is a need for more selective, specific, and stable nanoscale and microscale chemical sensor devices and methods for making and using them.

Recently, nanowires, nanotubes, and nanospheres as donors of electrical responses have been studied for the minimized nanostructures in the field of biosensors. Nanoscale biosensor devices can support in-vivo applications, and provide high sensitivity and detection at low concentrations (1). In addition, research on nanoscale biosensors has attempted to simplify detection by providing label-free, rapid, low-cost, multiplexed analysis. SWNTs are attractive materials for use in nanoelectronics (2-4). In particular, the electrical properties of SWNTs are good for use in advanced biological electronics and biosensors. Assembly of SWNTs and gold onto silicon wafers enables a high sensitivity electrical response for biosensors. Electrostatic or capillary methods are usually utilized for SWNT assembly onto silicon wafers, though their attachment to the silicon wafer is weak. Therefore, methods are required to maintain intact, assembled SWNTs are required. The use of SWNT-based chemiresistive/field-effect transistor (FET) sensors has been applied to medical sensor in-vitro systems (5-6). However, FET devices require three electrodes (working, reference, and counter electrodes), and their large size is hard to apply as an in-vivo medical detection system, although such devices can provide high sensitivity detection of target materials.

Miniaturized biosensors should detect and quantify small molecules with high sensitivity and selectivity. A variety of electrode modifications have been used for the immobilization of biomolecules onto SWNTs with covalent or non-covalent bonding methods. Covalent bonding methods using SWNT modification with chemical functional groups is associated with severe problems regarding SWNT electrical properties, because such methods can change (7-8). On the contrary, non-covalent bonding methods using $\pi$-$\pi$ stacking do not enable the transfer of chemical characteristics because they only utilize physical forces to immobilize materials onto SWNTs. Enzyme immobilization is also an important process for increasing the sensitivity and stability of biosensors. However, immobilized enzymes typically have low activity due to differences in local pH or electrostatic interactions at the matrix-enzyme interface, changes in overall enzyme structure resulting from covalent linkage, or matrix-induced confinement that decreases enzyme mobility available for conformation changes during substrate catalysis (9-11). Thus, there is a need to develop improved functionalization of SWNT using enzymes.

Further, there is a need to develop simple, sensitive, and stable biosensors with small footprint for the measurement of physiological markers, such as glucose, lactate, and urea in body fluid samples.

SUMMARY OF THE INVENTION

The invention provides microscale sensors for specifically detecting a chemical agent, methods for making the sensors, and methods of using the sensors to detect a chemical agent. The sensors and methods are well suited for use as a physiological biosensor, for example, of glucose, lactate, and urea. A "microscale" sensor as used herein refers to a sensor whose largest dimension or whose diameter is in the range of less than 1000 microns, or in certain embodiments less than 200 microns, less than 100 microns, less than 50 microns, less than 20 microns, or even less than 10 microns. Certain embodiments of the invention can be in the nanoscale range, less than 1 micron in size. The sensors are capable of detecting and quantifying chemical agents, such as glucose, lactate, and urea, or other enzyme substrates, at a wide range of physiologically relevant concentrations. The sensors of the invention are capable of specific detection of chemical agents, such that their exposure to other chemical agents produces a signal of only 20% or less, 10% or less, or 5% or less, or even 1% or less than that of the specifically detected chemical agent.

One aspect of the invention is a microscale biosensor for detecting a chemical agent. The biosensor includes a substrate, a conductive layer attached to a surface of the substrate and forming at least one pair of electrodes with an insulating gap between the electrodes, and a conductive bridge. The conductive bridge contains or consists essentially of one or more functionalized single-walled carbon nanotubes contacting the electrodes and bridging the gap between the electrodes. The one or more nanotubes are functionalized via a linker with an enzyme that reacts and with the chemical agent, whereby the conductivity or resistance of the conductive bridge is modified. The linker is preferably 1-pyrenebutanoic acid succinimidyl ester or a similar chemical compound, capable of both non-covalently associating with or binding to the SWNT, such as through $\pi$-$\pi$ interactions, and covalently bonding with a reactive group on an enzyme protein molecule, such as a free amino group.

In an embodiment of the biosensor, the SWNTs are semiconducting SWNTs. In an embodiment, the biosensor further comprises a circuit for receiving and/or processing of an electrical signal from said electrodes, such as an amperometry circuit, or a circuit containing an amperometry module. In an embodiment, the biosensor further comprises a transmitter for sending data obtained by the biosensor to a remote receiver.

In certain embodiments, the biosensor contains a plurality of conductive bridges, each formed of one or more functionalized single-walled carbon nanotubes, and each bridging a gap between a separate pair of said electrodes. In certain embodiments, the plurality of conductive bridges comprises single-walled carbon nanotubes functionalized with two or more different enzymes, and the biosensor is a multiplex biosensor capable of detecting two or more different chemical agents. In an embodiment, the biosensor specifically detects two or more chemical agents selected from the group consisting of D-glucose, L-lactate, and urea, or detects all of D-glucose, L-lactate, and urea simultaneously.

In certain embodiments, the biosensor is configured for implantation within a subject, such as within a blood vessel or space within an organ or tissue, or on the skin, and providing continuous or periodic detection of said chemical agent. In certain embodiments, the biosensor is configured for accepting a body fluid sample of a subject. The body fluid is, for example, blood, plasma, serum, sputum, urine, sweat, or another body fluid from a human subject or an animal. In certain embodiments, the biosensor further contains one or more microfluidic pathways for presenting the body fluid sample to the functionalized conductive bridge of the sensor. In embodiments, the biosensor provides quantification of a level, such as a concentration or amount, of the chemical agent. In embodiments the reaction of the chemical agent the enzyme results in increased electrical resistance of the conductive bridge.

Another aspect of the invention is a method of fabricating a biosensor. The method includes the steps of: (a) providing a substrate comprising a nanoscale trench; (b) depositing by fluidic assembly a conductive bridge consisting essentially of one or more single-walled carbon nanotubes into the nanoscale trench, the bridge having first and second ends; (c) depositing first and second conductive electrodes onto the substrate, whereby the first electrode covers and contacts the first bridge end and the second electrode covers and contacts the second bridge end; (d) associating 1-pyrenebutanoic acid succinimidyl ester as a linker with said single-walled carbon nanotubes and removing from the nanotubes any non-associated linker molecules; (e) reacting an enzyme with said nanotube-associated linker; and (f) blocking unreacted nanotube-associated linker using a reagent comprising free amino groups, to obtain the biosensor.

In embodiments of the method, the enzyme is selected from the group consisting of glucose oxidase, lactate oxidase, and urease.

Certain embodiments of the method include adding one or more microfluidic pathways and/or chambers onto said substrate and covering said conductive bridge.

In some embodiments of the method, two or more conductive bridges are deposited, each into a separate nanoscale trench, and each bridge is subsequently encased within a separate microfluidic pathway; the two or more deposited conductive bridges are each functionalized with a different enzyme in step (e).

Yet another aspect of the invention is a method of fabricating a biosensor. The method includes the steps of: (a) providing a substrate comprising a nanoscale trench; (b) depositing first and second conductive electrodes onto the substrate, the electrodes separated by an insulating gap; (c) depositing by dielectrophoretic assembly a conductive bridge consisting essentially of one or more single-walled carbon nanotubes, the bridge having a first end contacting the first conductive electrode and a second end contacting the second conductive electrode; (d) associating 1-pyrenebutanoic acid succinimidyl ester as a linker with said single-walled carbon nanotubes and removing from the nanotubes any non-associated linker molecules; (e) reacting an enzyme with said nanotube-associated linker; and (f) blocking unreacted nanotube-associated linker using a reagent comprising free amino groups, to obtain said biosensor.

In embodiments of the method, the enzyme is selected from the group consisting of glucose oxidase, lactate oxidase, and urease. In embodiments, the method further includes adding one or more microfluidic pathways and/or chambers onto said substrate and covering said conductive bridge.

In yet other embodiments of the method, two or more conductive bridges are deposited in step (c), each by dielectrophoretic assembly between two conductive electrodes. In some embodiments, each bridge is subsequently encased within a separate microfluidic pathway, and the two or more deposited conductive bridges are each functionalized with a different enzyme in step (e), resulting in a multiplex biosensor. In some embodiments, each of the two or more conductive bridges is assembled using uniquely pre-functionalized single-walled carbon nanotubes, resulting in a multiplex biosensor.

Still another aspect of the invention is a method of detecting a chemical agent in a sample. The method includes the steps of: (a) measuring a baseline conductance, resistance, or current value of the conductive bridge of a biosensor in the absence of the sample; (b) exposing the conductive bridge to the sample; and (c) measuring a change in the conductance of the bridge in the presence of the sample compared to the absence of the sample, wherein the change in conductance indicates the presence or absence of the chemical agent in the sample.

In certain embodiments of the method, values of a parameter such as conductance, resistance, or current values from the biosensor are transmitted to a remote receiver. In certain embodiments, the biosensor is a multiplex biosensor and data are transmitted or processed for a plurality of chemical agents simultaneously. In some embodiments, a diagnosis, prognosis, or treatment recommendation is output or transmitted by the biosensor.

DETAILED DESCRIPTION OF THE INVENTION

The invention provides a highly sensitive, stable biosensor capable of detecting physiological markers using an enzyme immobilized on single-walled carbon nanotubes (SWNT) for detecting physiological substrates of the immobilized enzyme (e.g., D-glucose, L-lactate, or urea) in-vivo. The biosensor has a smaller footprint than conventional FET-based sensors, taking advantage of the conductive electrical property of SWNTs for the detection and quantification of substrates such as D-glucose, L-lactate, and urea. The biosensor takes advantage of a 1-pyrenebutanoic acid succinimidyl ester (PBSE) linker, which attaches non-covalently to SWNT by means of $\pi$-$\pi$ interactions via the pyrene moiety on the one hand, and covalently to amino groups of an enzyme protein molecule via the succinimide group on the other hand. This linker allows enzyme reactions to disturb conductance through the SWNT of the sensor, producing a readily detectable increased resistance. The linker can be used to functionalize SWNT with glucose oxidase (GOD), lactate oxidase (LOD), or urease (URE), for example.

Figure 1:
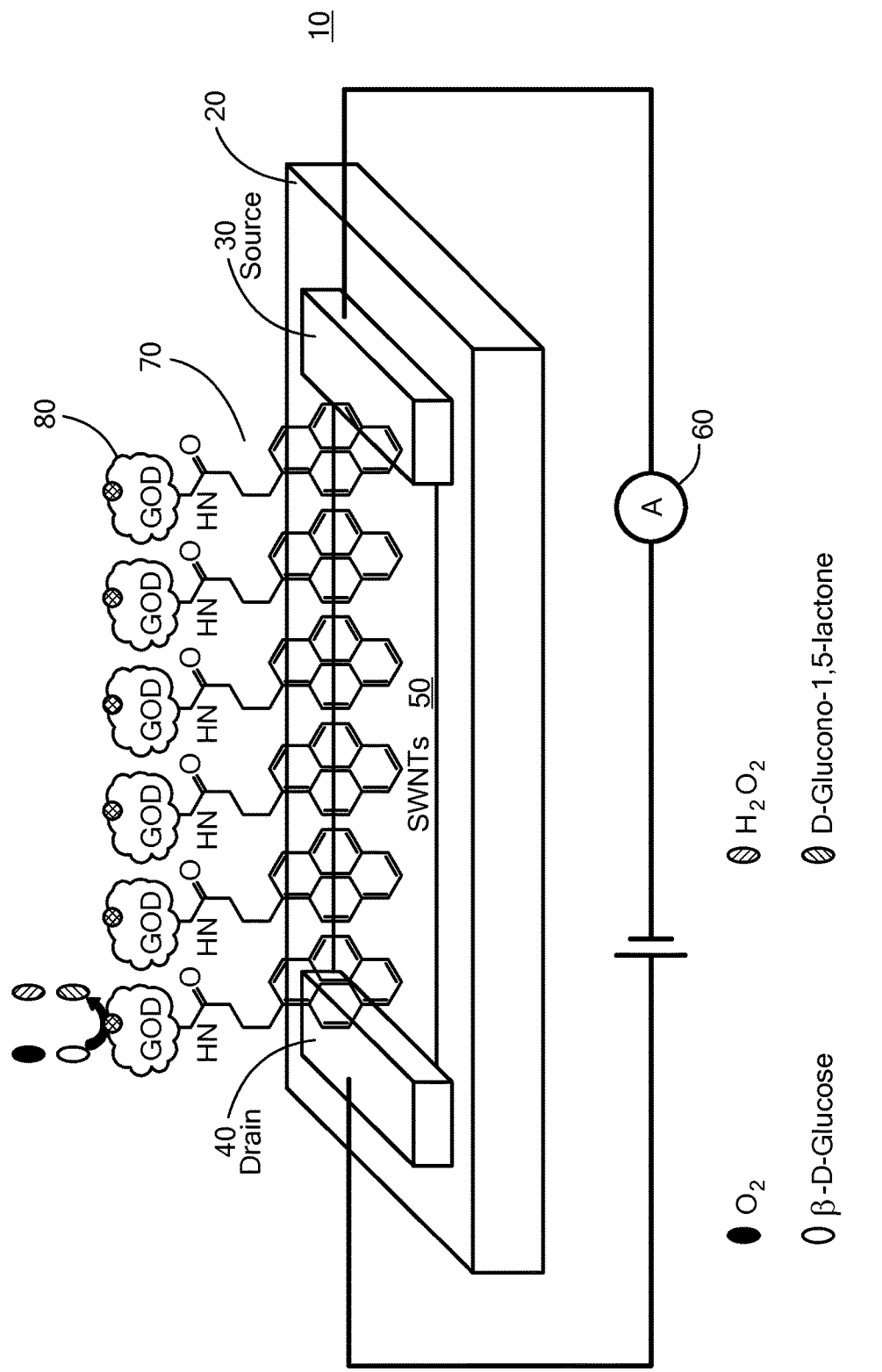
FIG. 1 shows a schematic diagram of an embodiment of a biosensor for glucose according to the invention.

FIG. 1 schematically depicts a sensor device according to the invention. SWNTs serve as an active channel layer because of their extremely high surface area to volume ratio and lack of direct chemical interaction with most physiological substrates that might interfere with detection of molecules of interest, such as glucose, lactate, and urea. Biosensor 10 includes substrate 20, which is electrically insulating, such as silicon dioxide coated silicon. SWNT bundle 50 is deposited as a linearly ordered assembly stretching or bridging between electrical contacts 30 and 40, which can be, for example, gold pads deposited on the substrate directly, or upon the ends of the SWNT bridge and the substrate. The contacts or electrodes are connected to circuit 60, such as and an amperometry circuit mounted within the device or externally. Linker moiety 70 is preferably 1-pyrenebutanoic acid succinimidyl ester (PBSE) or a similar linker molecule, having a pyrene or other $\pi$-bonding aromatic group at one end and an amino-reactive group on the other end. An enzyme 80 (here exemplified is glucose oxidase (GOD)) is covalently attached to the PBSE linker.

Figure 2:
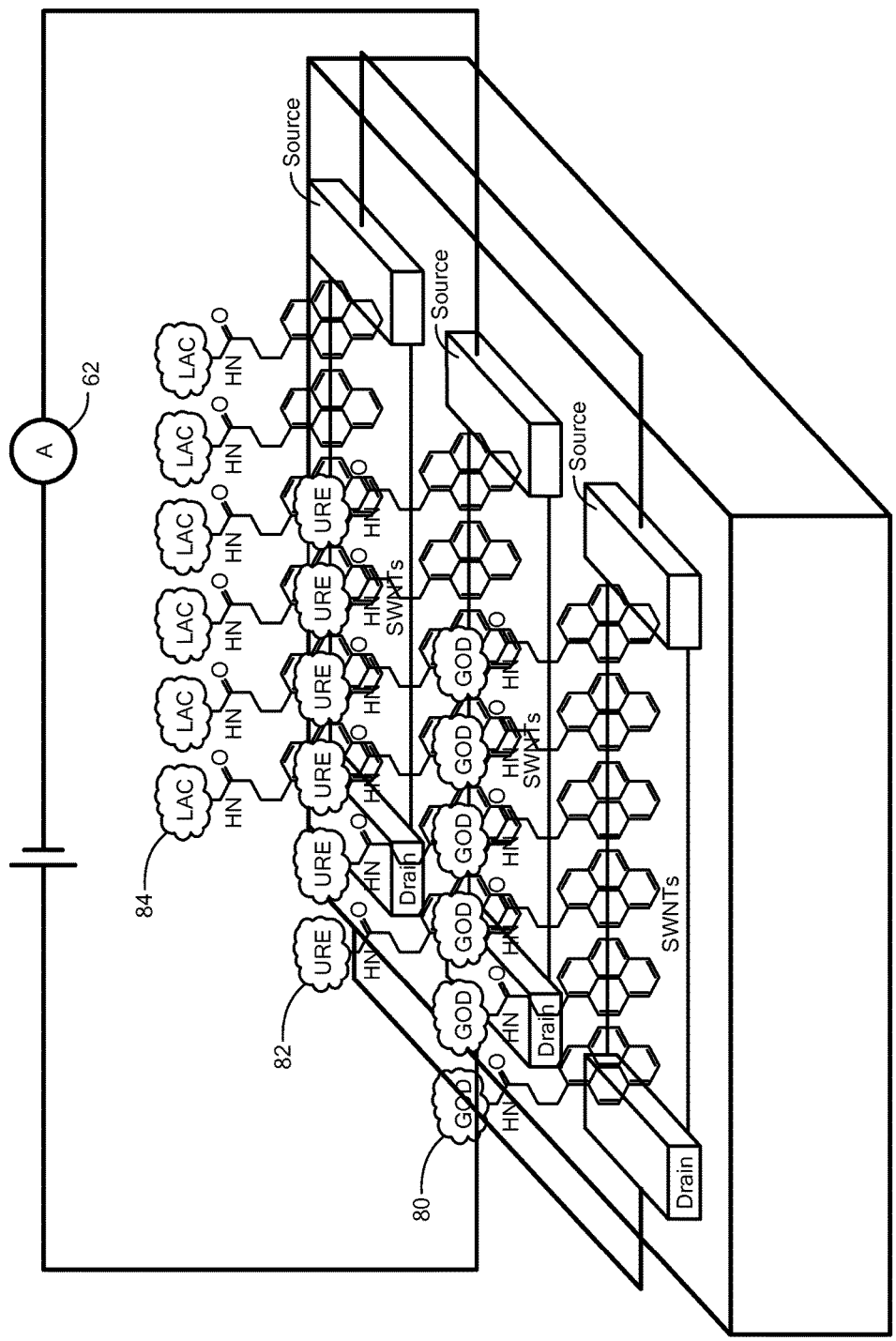
FIG. 2 shows a schematic diagram of an embodiment of a multiplex biosensor for glucose, urea, and lactic acid according to the invention.
Figure 3A:
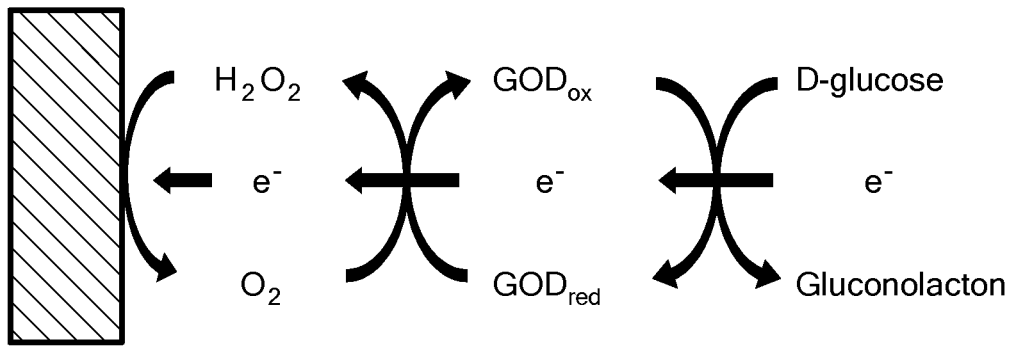
FIG. 3A shows a D-glucose detection mechanism using SWNT-immobilized glucose oxidase enzyme.
Figure 3B:
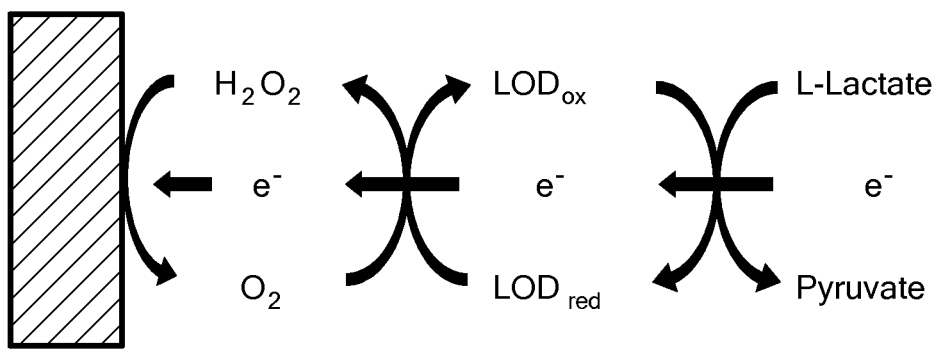
FIG. 3B shows an L-lactate detection mechanism using SWNT-immobilized lactate oxidase enzyme.
Figure 3C:
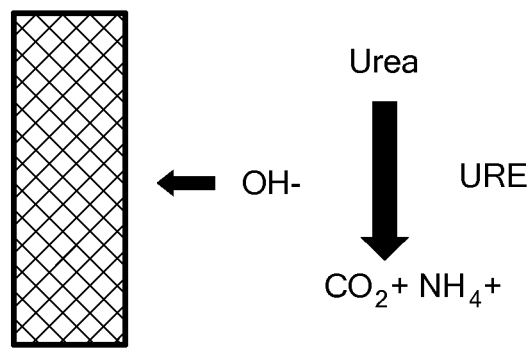
FIG. 3C shows a urea detection mechanism using SWNT-immobilized urease enzyme.

An example of a multiplex sensor device is shown in FIG. 2. In this embodiment, which is designed for assay of metabolic parameters involving glucose (detected by glucose oxidase 80), lactate (detected by lactate oxidase 82), and/or urea detected by urease (84), the sensor chip is electrically linked to a multiplexer circuit and data transmission chip via one or more electrical connections. Data from the sensors are transferred to the circuit, where they can be optionally processed and subsequently transmitted to a remote receiver. FIGS. 3A-3C show the chemical reactions carried out by the respective enzymes in this multiplex biosensor embodiment.

Figure 4A:
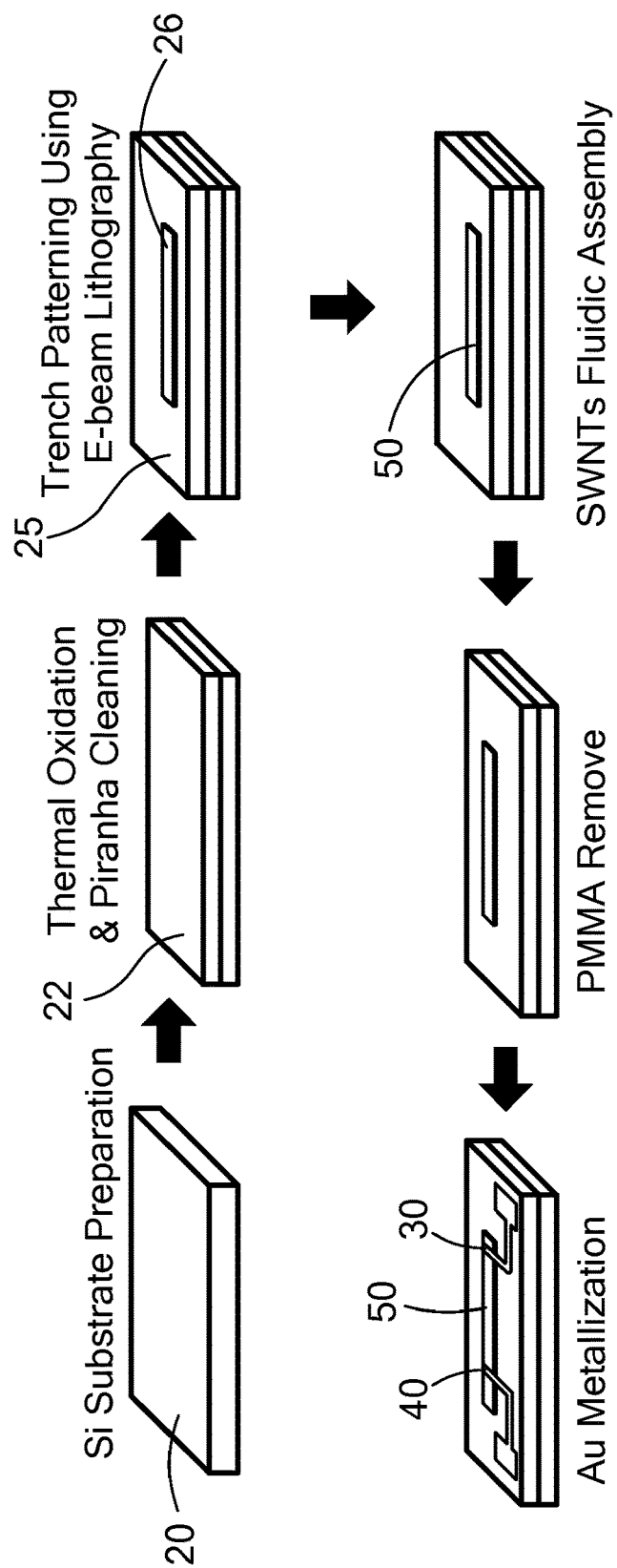
FIG. 4A shows a schematic diagram of an embodiment of a fluidic assembly process for fabricating a biosensor.
Figure 4B:
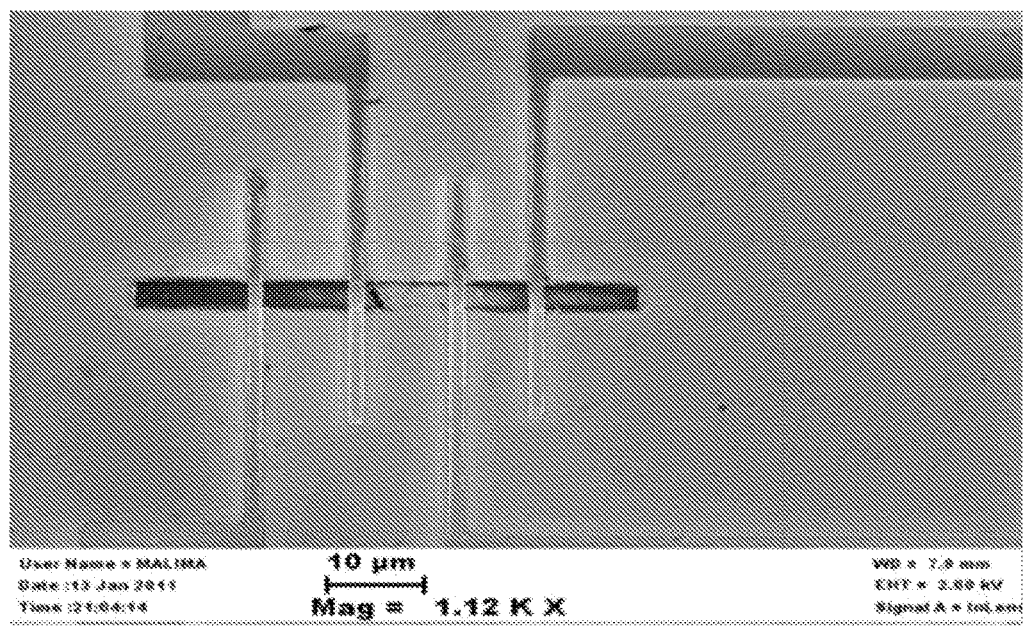
FIG. 4B shows an SEM image of a biosensor produced by the method shown in FIG. 4A.
Figure 4C:
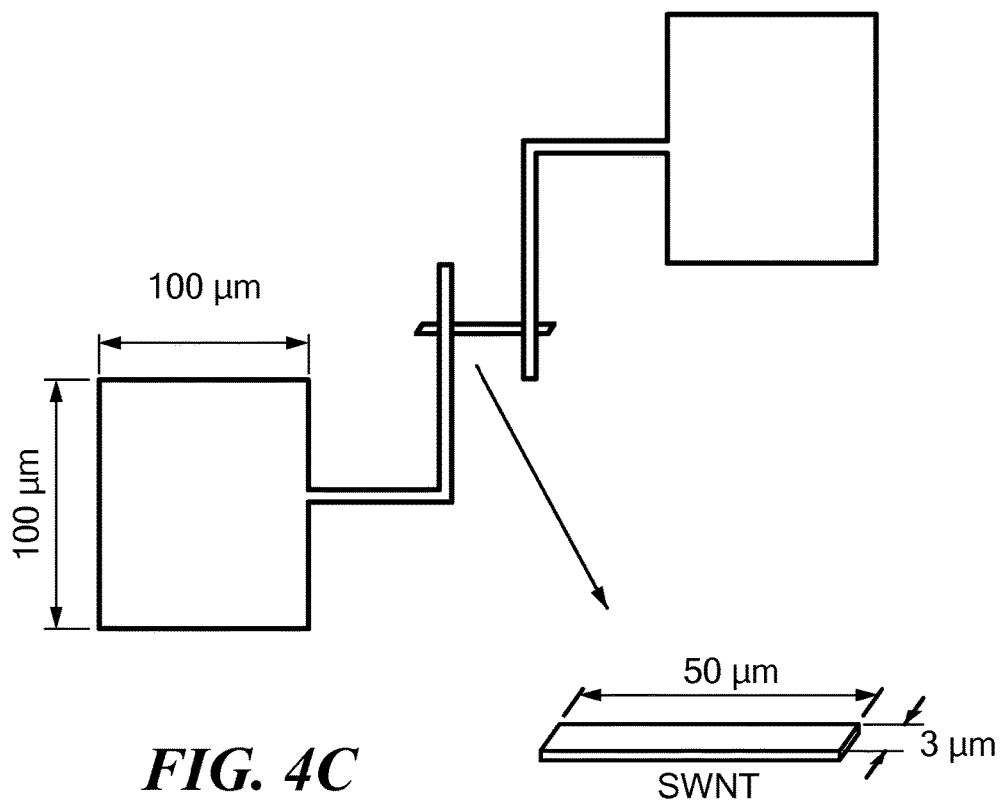
FIG. 4C shows a schematic diagram of the biosensor in FIG. 4B; the expanded view illustrates the dimensions of the assembled SWNT bundle.
Figure 5A:
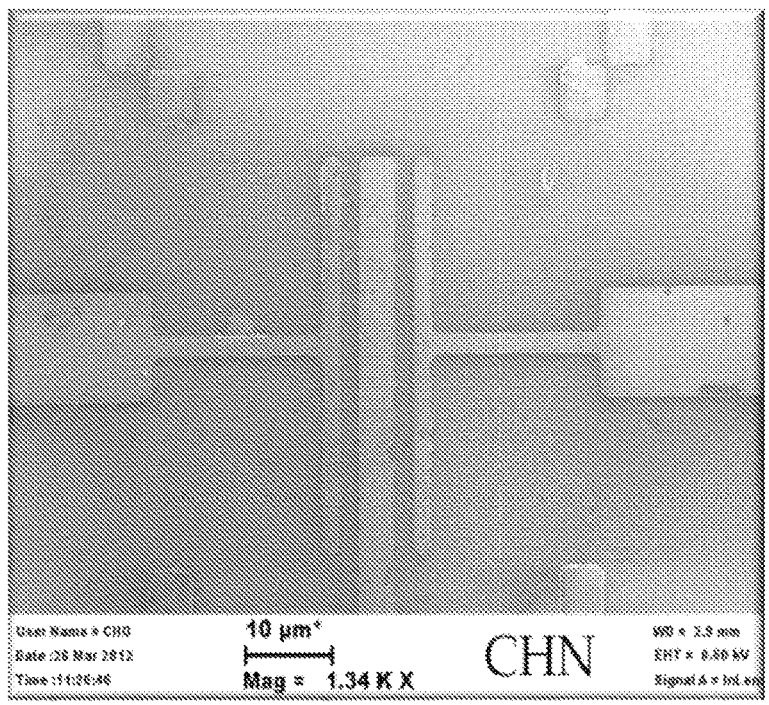
FIG. 5A shows an SEM image of a biosensor device assembled using dielectrophoretic assembly of SWNT onto gold contact pads.
Figure 5B:
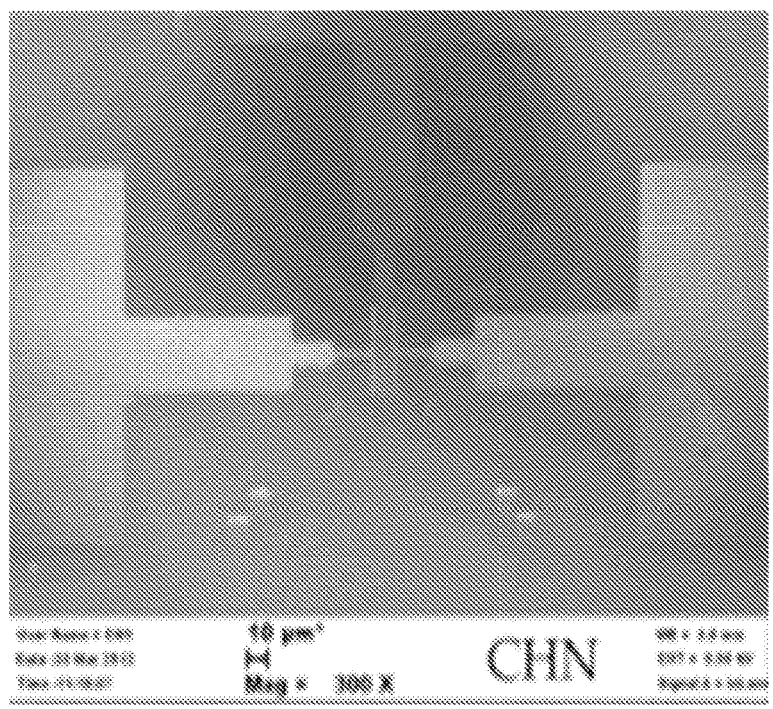
FIG. 5B shows a lower magnification image of the device shown in FIG. 5A.

One possible fabrication sequence of a functionalized SWNT biosensor is shown in FIG. 4A. Directed assembly of SWNTs is performed following microfabrication procedures to fabricate the device. SWNT can be functionalized by depositing the functionalizing agent (linker and enzyme) onto the SWNT, either prior to or following assembly in the sensor. Preferably, the SWNT are functionalized by incubating SWNT in suspension together with a linker that adheres non-covalently to the SWNT, interacting with sidewalls of the SWNT by means of hydrophobic interactions and/or pi-stacking interactions. Preferred methods of non-covalently coating the SWNT with the linker include drop coating, spin coating, sublimation, and evaporation or vaporization. The linker is then reacted with the desired enzyme, following which unreacted groups on the SWNT-attached linker are blocked. Alternatively, the already assembled SWNT can be functionalized by covering them with a solution containing the linker, and subsequently reacting the linker with the enzyme, or by covering the SWNT with a solution of linker pre-reacted with enzyme. The base of the sensor is an electrically insulating substrate of a material such as Si, $SiO_2$, or a combination thereof (e.g., a base of silicon coated with a layer of $SiO_2$). One or more pairs of electrodes are deposited on the substrate using conventional techniques. For example, a mask layer can be applied to the substrate and patterned using lithography (e.g., photolithography, electron beam lithography, or ion beam lithography), followed by deposition of a conductive layer (e.g., a layer of gold, silver, chromium, or another electrically conductive metal, or any combination thereof) to form the electrodes, optionally with an adhesion layer deposited between the substrate and the conductive layer. A gap of insulating material (e.g., bare substrate material) is left between each pair of microelectrodes. The SWNT are assembled into bundles that form electrical contact with the two electrodes of a pair, one electrode at each end of the bundles; the bundles of SWNT bridge the insulating gap and provide a current path between the electrodes. Any method of assembling the nanotubes can be used. A preferred method is the fluidic assembly method which is described in Jaber-Ansari et al., J. Am. Chem. Soc. 131, 804-808 (2009) and U.S. published patent application 2010/0183844, which is hereby incorporated by reference. An actual device fabricated by the fluidic assembly method is shown in FIG. 4B (SEM image), and schematically in FIG. 4C. An alternative method is by dielectrophoretic assembly, in which a suitable AC electric field is applied between two electrodes which determine the endpoints of the SWNT bridge to be formed. See, e.g., P. Makaram et al., Nanotechnology 18, 395204 (2007). An actual device fabricated using dielectrophoretic assembly is shown in FIGS. 5A and 5B. After assembly, the nanotube bundles form a conductive bridge between the electrodes. In one embodiment, the SWNT are predominantly semiconducting. SWNT. The completed sensor device responds to interaction of the chemical agent for which it is designed with the functional group by altering the conductance (therefore also the resistance) of the SWNT bridge.

The resistance changes in the device are dependent the number of contacts of the elements within the network. Molecular interactions disrupt the network continuity resulting in increased resistance. Percolation phenomena are determined by the concentrations of conductive materials in the system. Therefore, a high SWNT concentration leads to good current flow, while the modified SWNTs inhibit the percolation and result in the increased resistance (15).

The resistance of a bundle or an array of SWNT is modified upon the chemical interaction of a specific functional group by a chemical agent whose detection is desired. The altered resistance provides a signal that registers the presence and/or concentration of the chemical agent in the environment of the sensor. For example, SWNTs modified with a glucose oxidase enzyme can serve as a conduction channel that is sensitive to glucose. The channel dimensions and the functional group loading values are defined by the sensitivity window provided by the functional group, such as the affinity of the glucose oxidase enzyme for glucose. The sensitivity and electrical response characteristics are also influenced by the dimensions of the channel in which the SWNT are deposited. A preferred channel has dimensions of about 1 micron in width by about 10 microns in length, although any desired dimensions can be used. Larger channels will produce a larger signal. Channels are preferably in the general form of an elongated rectangle, having a width smaller than the length, but other shapes can be used. The SWNT deposited in a channel are in electrical contact with electrodes at both ends of the channel, and the two electrodes are electrically connected to a circuit, thus forming a two-wire circuit that can be used to measure the resistance or conductance of the SWNT as a function of time. The interaction or exposure of these sensors to the chemical agent of interest result in a measurable change (decrease or increase) in the current flowing through the SWNT channel, which is a signature of the presence of the chemical agent. By providing different enzymes, the chemical sensor of the invention can be made specific for a variety of different chemical agents, namely the enzyme substrates.

In certain embodiments the sensor is a multiplex sensor, having two or more sections each devoted to detection of a different chemical agent or class of chemical agents. The multiplex sensor embodiment utilizes a differently functionalized SWNT set to detect each corresponding chemical agent. In one embodiment, the multiplex sensor can include one or more sensors for D-glucose, L-lactate, and urea that can affect one or more biochemical sensors on the device. The multiplex sensor can be configured so as to contain two or more sections, each of which detects a different chemical agent, because each section contains a set of distinctly functionalized SWNT and is connected to a different set of circuitry. In order to fabricate such a multiplex sensor, each section can be fabricated in a separate process, and the complete set of sensor sections can be fabricated sequentially. For example, a first sensor section, capable of detecting $agent_1$, can be fabricated by performing lithography on the substrate to prepare a set of channels for $SWNT_1$ deposition, and functionalized $SWNT_1$ are deposited in those channels. Alternatively, non-functionalized SWNT can be deposited and then functionalized in situ to create $SWNT_1$ by adding one or more reagents to the deposited SWNT so as to add functional $group_1$ to the SWNT. Subsequently, a second sensor section, capable of detecting $agent_2$, can be added to the sensor to form a multiplex sensor. A second set of channels is then added to the sensor by photolithography, which is performed in a manner that does not disturb the already formed first sensor. $SWCNT_2$ are then added to the second set of channels as before, adding the capability to detect $agent_2$ simultaneously with detection of $agent_1$. Alternatively, a microfluidic embodiment can be prepared, offering fluidic access to different channels individually. Still another method is to add SWNT by dielectrophoretic assembly to individual channels which can be accessed to provide a directed electric field to drive assembly in only desired channels. Using such approaches, fabrication can continue to add as many differently functionalized sensor sections as desired. For example, 2, 3, 4, 6, 8, 9, 10, 12, 15, 20, 100, 1000, or more separate sensor sections can be added to the multiplex sensor.

One of the major findings with multiplex biosensors of the present invention was that enzyme-immobilized semiconducting SWNTs using non-covalent bonding with highly electrically sensitive SWNT conductance provided good detection of D-glucose, L-lactate, and urea with high repeatability (10, 9, and 9 times), stability (14, 9, 14 days) and sensitivity (0.005 µM, 0.001 mM, and 0.001 g/dL detection limits) respectively, while there was no effect of other biomolecules on the detection of each intended substrate. In addition, due to its inherent small size, the biosensor can be used for in vivo mode applications. The biosensor was able to detect D-glucose, L-lactate, and urea over the large ranges of 0-300 µM, 0-100 mM, and 0-100 g/dL, respectively. These ranges are sufficient to provide physiological monitoring in a blood tube.

In addition, the sensors according to the invention can serve as a platform for the development of multifunctional sensors, to perform, for example, simultaneous measurements of many metabolic and/or disease markers on a single chip. Incorporation of read out electronics, one or more optional RF signal generators and one or more optional multiplexers into a chip containing the biosensors would enable them to communicate to a main relay station (e.g., in a laboratory), which in turn can transmit the data to a remote receiver for other analysis. Implementation of simple algorithms also can be used to retrieve the signal from these sensors with position and time information.

EXAMPLES

Example 1

Fabrication of a Biosensor Using Dielectrophoretic Assembly of SWNT

In one exemplary fabrication process, gold pads were fabricated on a thermally oxidized (1 µm thick) silicon wafer as a substrate. A conventional piranha cleaning process ($H_2SO_4:H_2O_2$; 4:1) was used to clean organic residues off the substrate and also to hydroxylate the oxide surface and render it hydrophilic. As soon as the temperature of the solution reached 110° C., the substrate was submerged into the solution for 10 min. followed by de-ionized (DI) water rinse for 10 min. After the piranha cleaning was complete, the substrate was blow-dried with $N_2$ gas to remove the water.

After preparation of the substrate, a 600 nm thick layer of polymethylmethacrylate (PMMA) resist (950 PMMA A, Micro Chem., USA) was spin-coated on the substrate at 5000 rpm for 60 sec followed by baking at 160° C. for 90 sec on a hotplate. E-beam lithography was then used to generate 3×50 µm trenches (FIGS. 4A-4C) on the PMMA with a field emission scanning electron microscope (FE-SEM, Supra 25, Carl Zeiss Inc. USA). The exposed resist was then developed in a solvent (a mixture of methyl isobutyl ketone and isopropanol). A template guided dielectrophoretic assembly process was utilized to integrate SWNT with fabricated templates. SWNT were assembled on the template guided substrate using dielectrophoretic assembly by probe station. The templates were dipped in a DI water-based SWNT suspension and then 1.0 V of electric potential was supplied using a frequency of 1.0 MHz for 60 sec, a spacing of 800 nm between SWNT bridges. FIGS. 5A-5B show SEM images of an SWNT connection between gold pads fabricated by this method. The distance between gold pads was 1.0 µm, and the size of the whole device was 50×50 µm².

For the non-covalent functionalization and immobilization of GOD, LOD, and URE onto the assembled SWNT bundle, the templates were incubated with 6 mM 1-pyrenebutanoic acid succinimidyl ester (PBSE) as a linker in pure dimethylformamide (DMF) for 2 hr at room temperature. This was followed by rinsing with pure DMF and DI water to wash away any excess reagent. For the immobilization of GOD, LOD, and URE on the SWNT surface using covalent bonding, each SWNT bundle device was exposed to 1 mM of each enzyme in bicarbonate buffer (pH 7.4) overnight at room temperature. The device was then rinsed thoroughly in DI water and phosphate buffered saline (PBS, pH 7.4), and then dried with nitrogen ($N_2$) gas. To deactivate and block the excess PBSE reactive groups remaining on the SWNT surface, 100 mM ethanolamine was added onto the channel region of the device and incubated for 30 min. The PBSE-modified assembled SWNTs template was then rinsed with PBS buffer (pH 7.4).

Example 2

Effects of Enzyme Immobilization on SWNT Characteristics

Figure 6A:
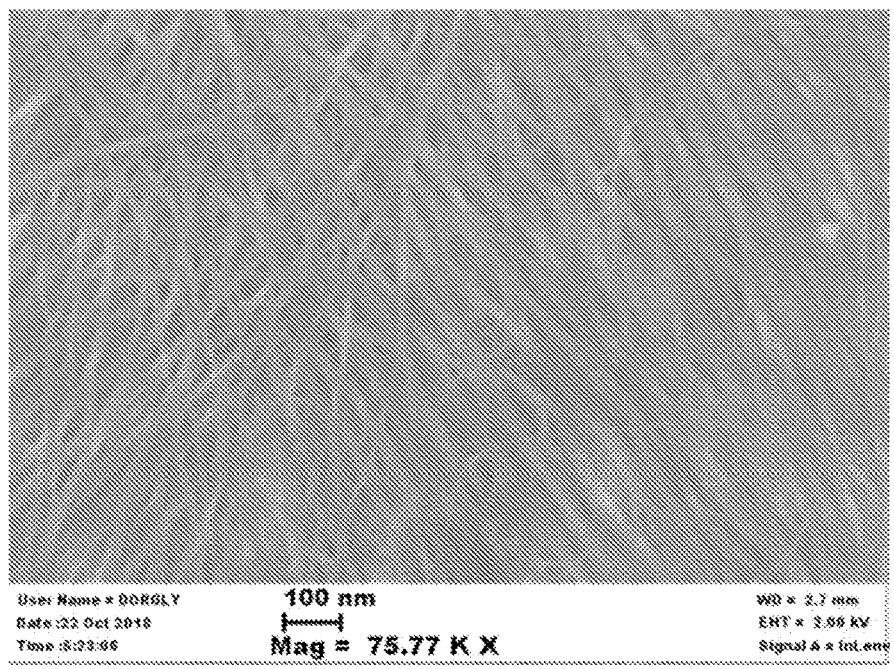
FIG. 6A shows an SEM image of bare (non-functionalized) SWNT assembled into a biosensor device using fluidic assembly.
Figure 6B:
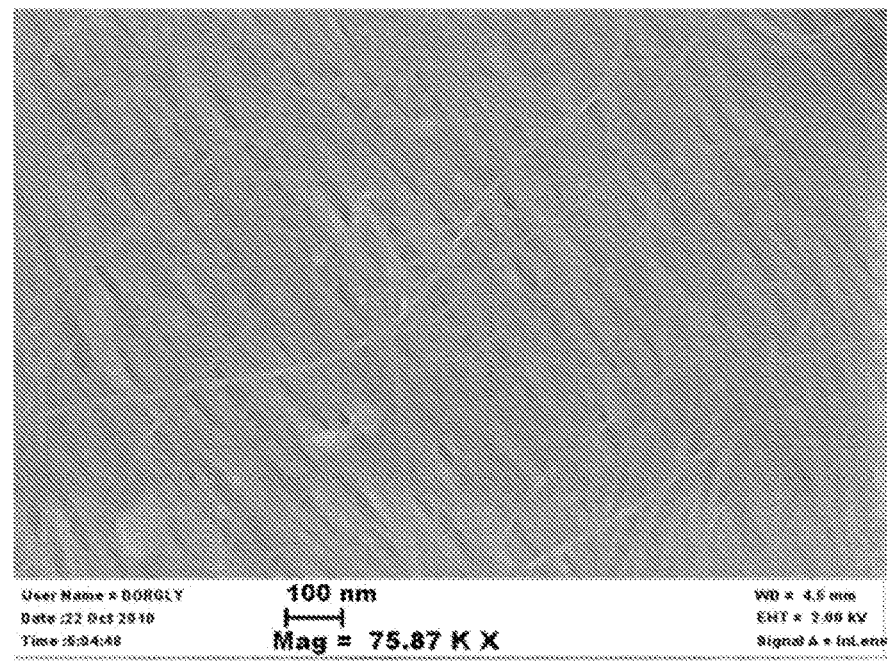
FIG. 6B shows a similar device having SWNT that are functionalized with glucose oxidase enzyme.
Figure 7A:
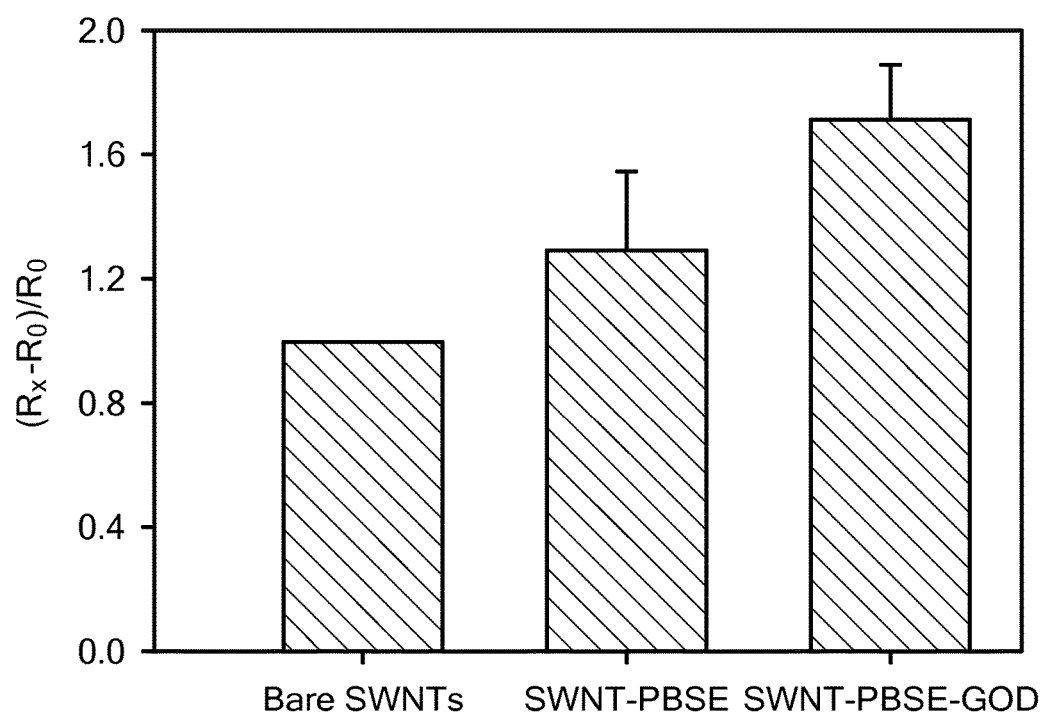
FIG. 7A shows the resistance of a biosensor fabricated by the method shown in FIG. 4A; the resistance is compared for the bare SWNTs, the SWNTs complexed with PBSE, and the SWNTs complexed with PBSE linked to glucose oxidase (GOD).
Figure 7B:
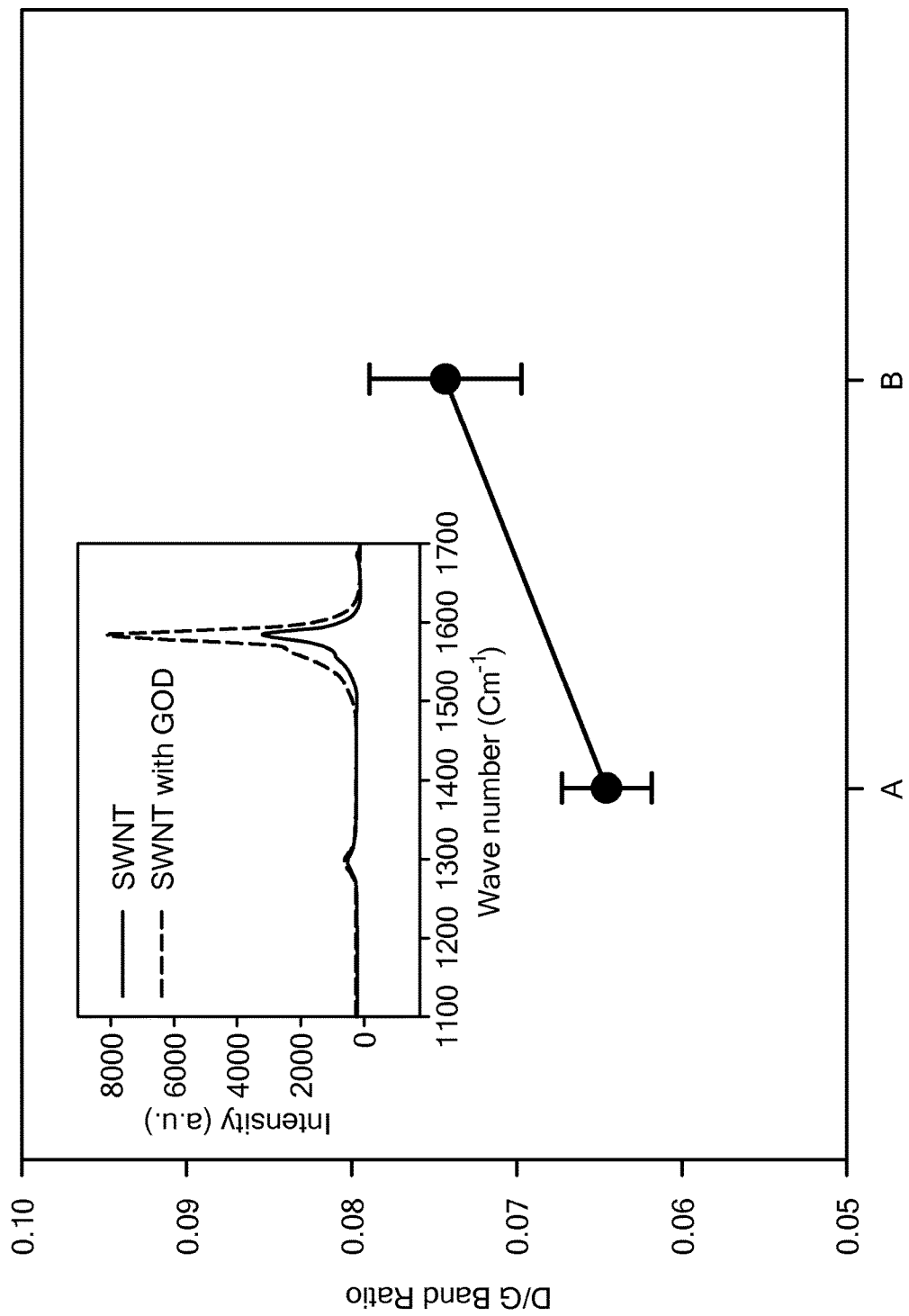
FIG. 7B shows the ratio of G/D bands in Raman spectrograms of the SWNT before (A) and after (B) immobilization of GOD with PBSE.

The enzyme immobilization process was defined using FE-SEM images (FIG. 6A-6B), resistance responses (FIG. 7A), and Raman spectra (FIG. 7B). A rougher surface on the SWNTs was observed in the FE-SEM images due to the presence of the immobilized glucose oxidase enzyme. In addition, the amount of empty space between SWNT bundles was decreased compared with bare SWNT bundles without glucose oxidase immobilization. The resistance changes in the device were dependent the number of contacts of the elements within the network, with resistance increasing from bare SWNTs to SWNTs with linker to SWNTs with linker and enzyme (FIG. 7A). Molecular interactions disrupt the network continuity, resulting in increased resistance. Percolation phenomena are determined by the concentrations of conductive materials in the system. Immobilized glucose oxidase was found to increase the ratio of G/D bands in Raman spectra from $6.45 \times 10^{-2}$ to $7.42 \times 10^{-2}$ (FIG. 17B).

Example 3

Resistance Response of a Glucose Oxidase-Functionalized Biosensor

Figure 10B:
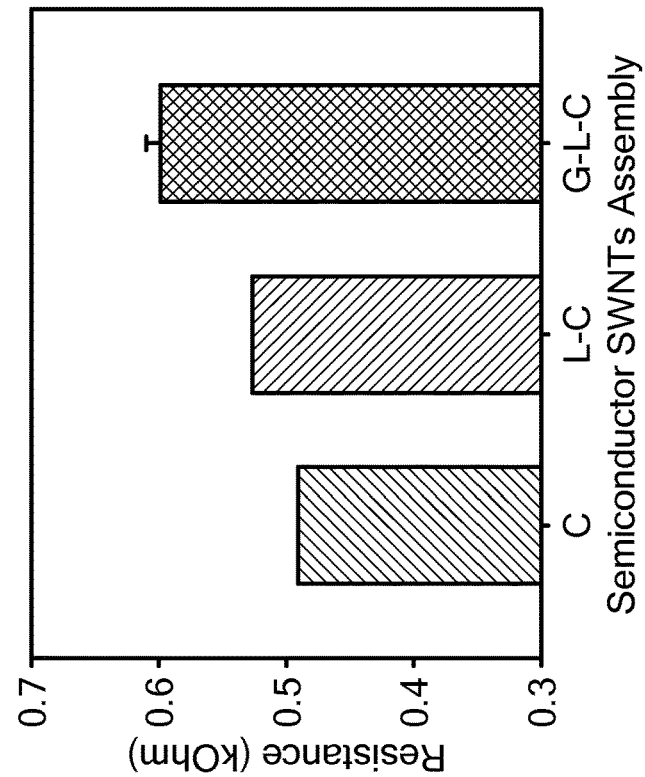
FIG. 10B shows the resistance response of semiconductor SWNT assemblies. For both FIGS. 10A and 10B, C represents SWNTs; L-C represents linker(PBSE)-SWNT, and G-L-C represents glucose oxidase-linker-SWNT.
Figure 10A:
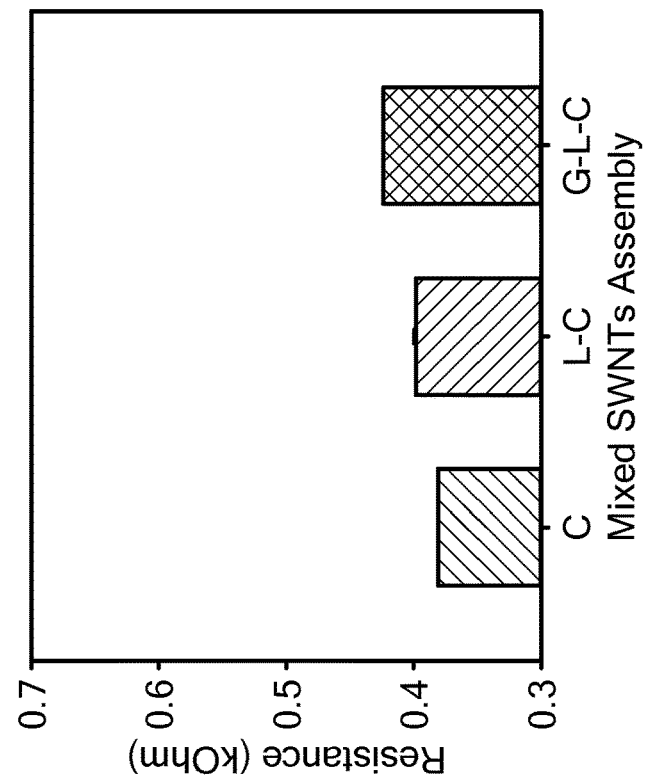
FIG. 10A shows the resistance response of metallic/semiconducting mixed SWNT assemblies.
Figure 11A:
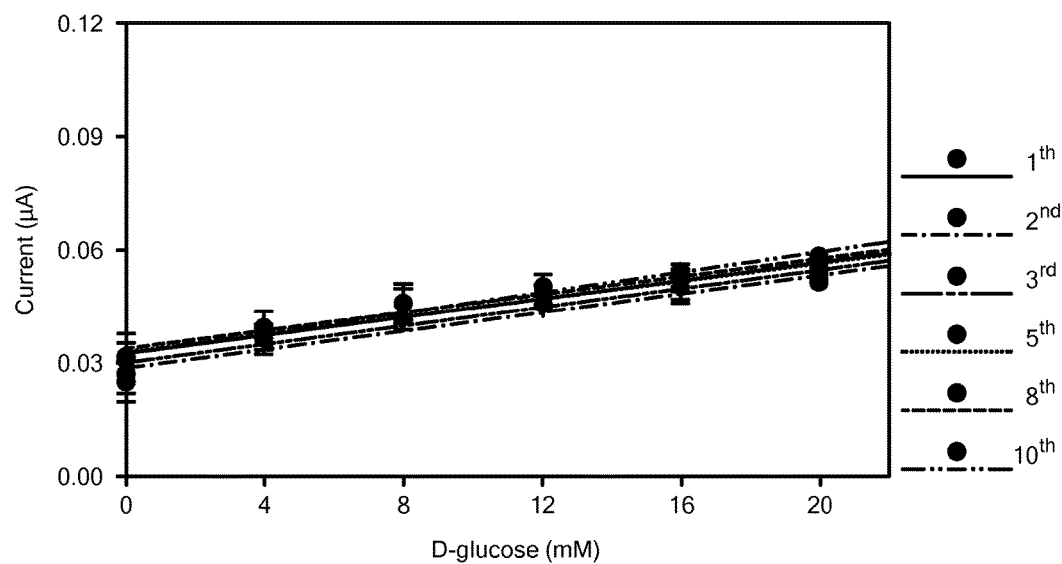
FIG. 11A illustrates the repeatability of a glucose oxidase-functionalized biosensor for D-glucose detection at the indicated D-glucose concentrations for 10 duplicate measurements.
Figure 11B:
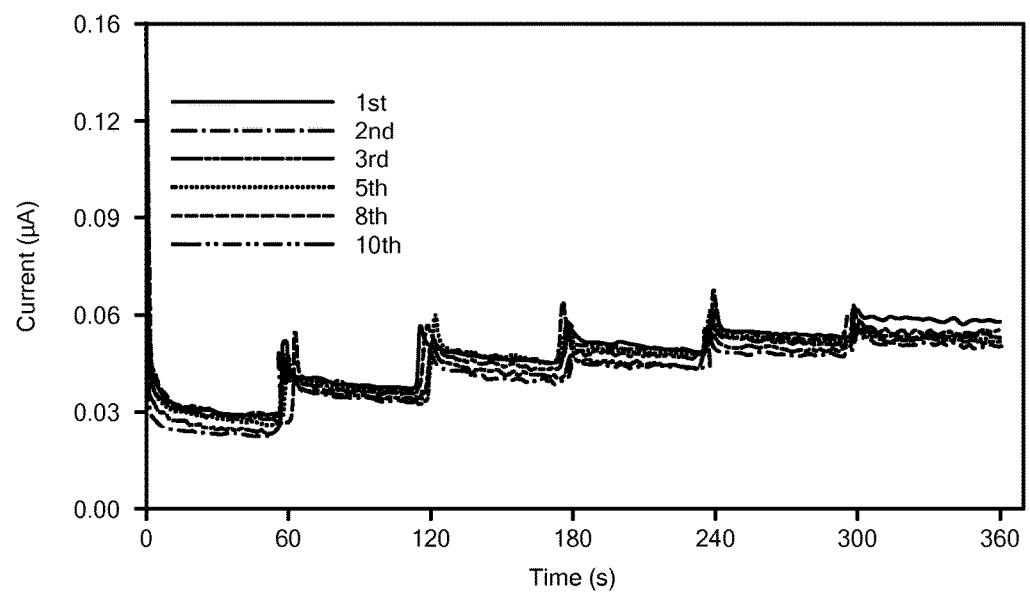
FIG. 11B illustrates the time course of D-glucose detection for the data shown in FIG. 11A.
Figure 11C:
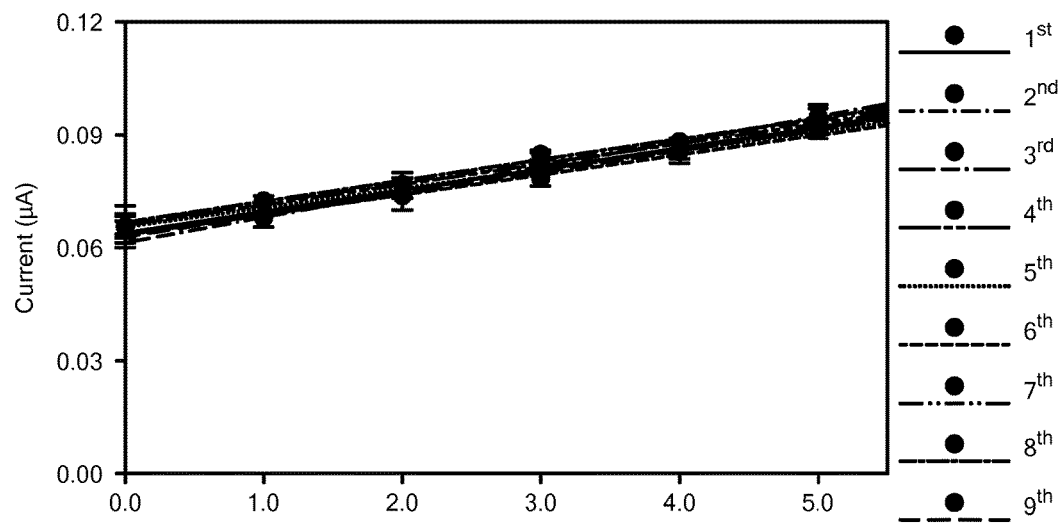
FIG. 11C illustrates the repeatability of a lactate oxidase-functionalized biosensor for L-lactate detection at the indicated L-lactate concentrations for 10 duplicate measurements.
Figure 11D:
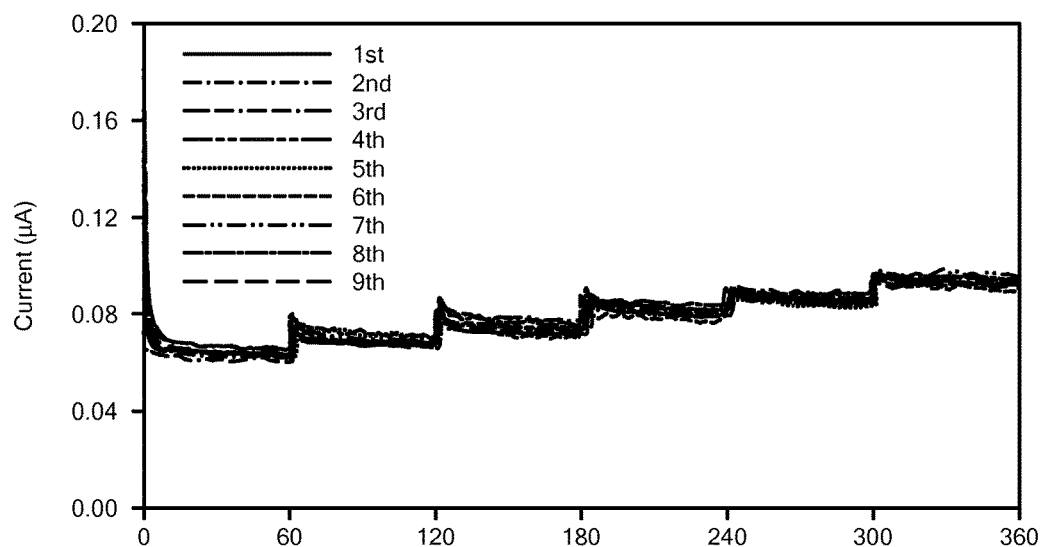
FIG. 11D illustrates the time course of L-lactate detection for the data shown in FIG. 11C.
Figure 11E:
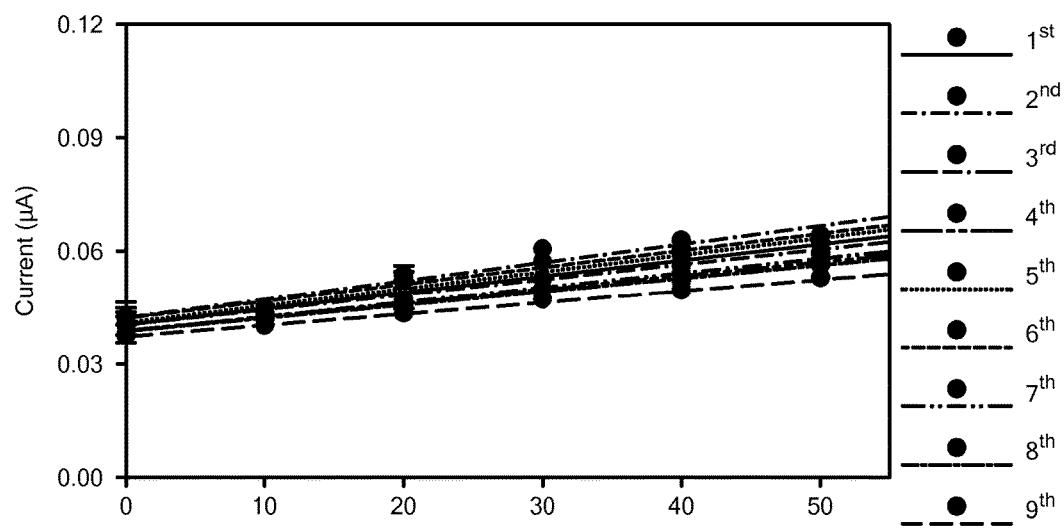
FIG. 11E illustrates the repeatability of a urease-functionalized biosensor for urea detection at the indicated urea concentrations for 10 duplicate measurements.
Figure 11F:
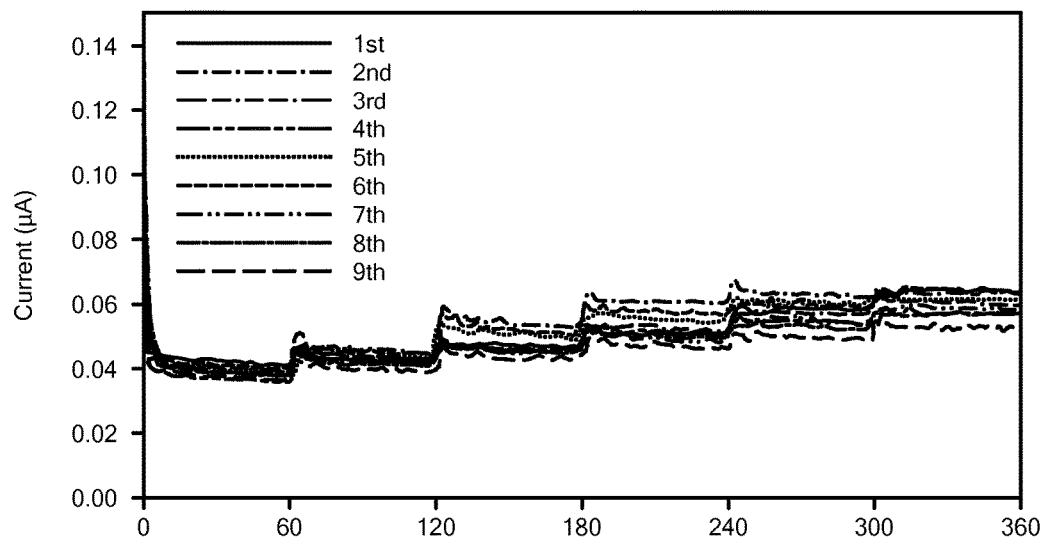
FIG. 11F illustrates the time course of urea detection for the data shown in FIG. 11E.
Figure 12A:
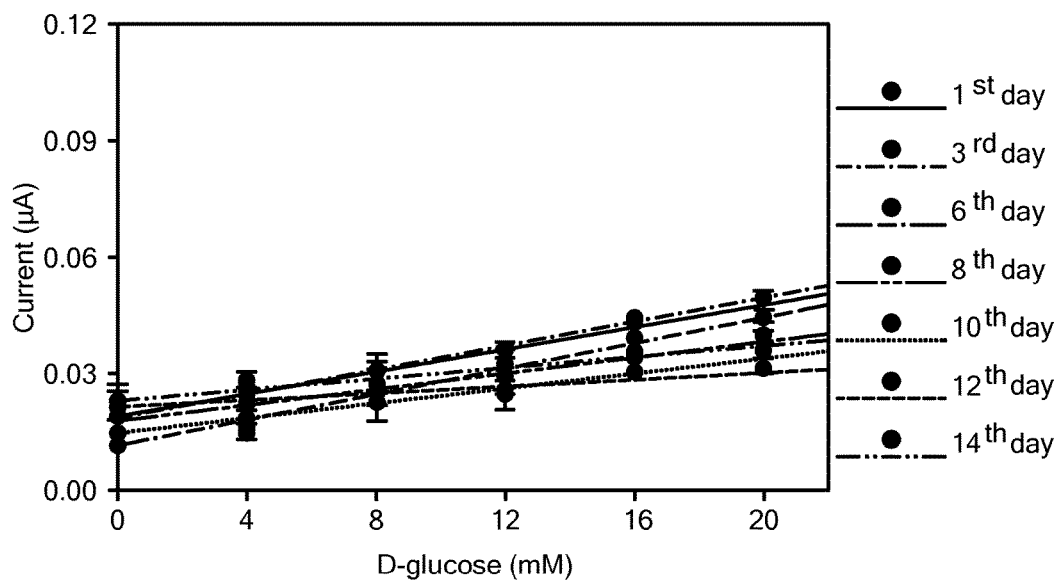
FIG. 12A illustrates the stability of the glucose oxidase-functionalized SWNT biosensor for D-glucose detection.
Figure 12B:
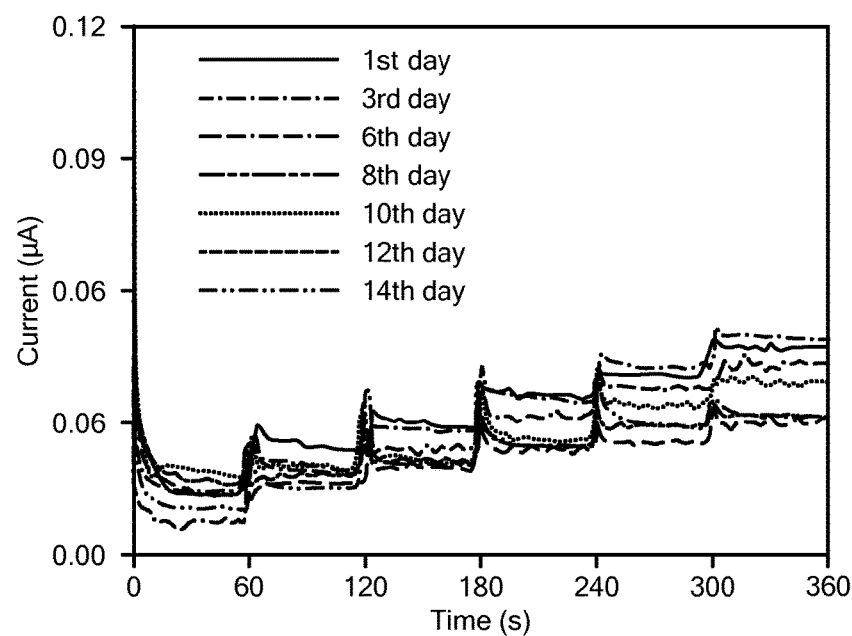
FIG. 12B illustrates the time course of D-glucose detection for the data shown in FIG. 12A.
Figure 12C:
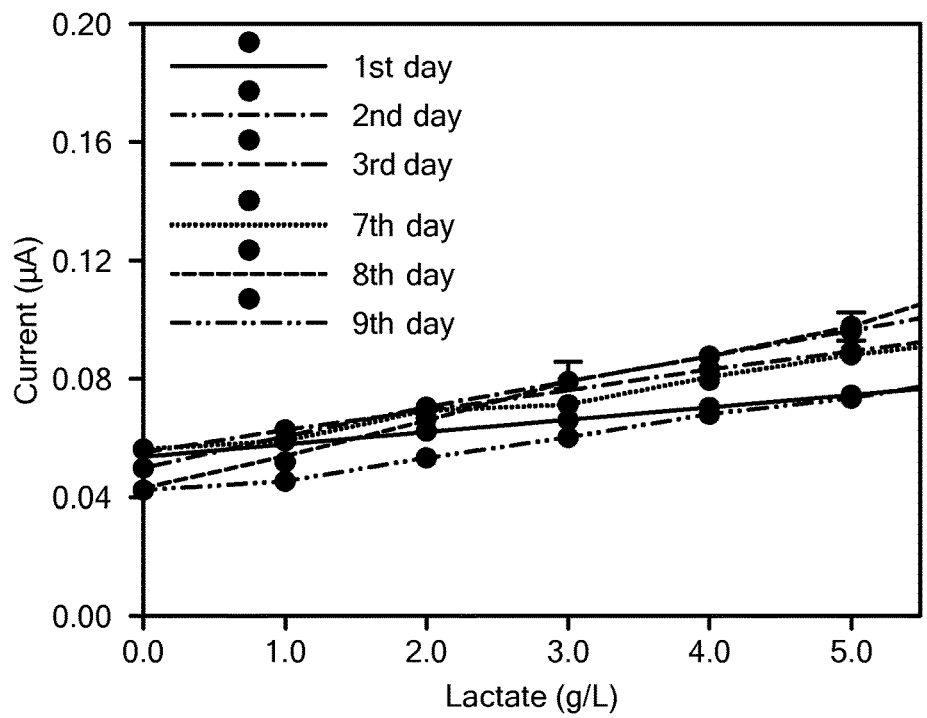
FIG. 12C illustrates the stability of the lactate oxidase-functionalized SWNT biosensor for L-lactate detection.
Figure 12D:
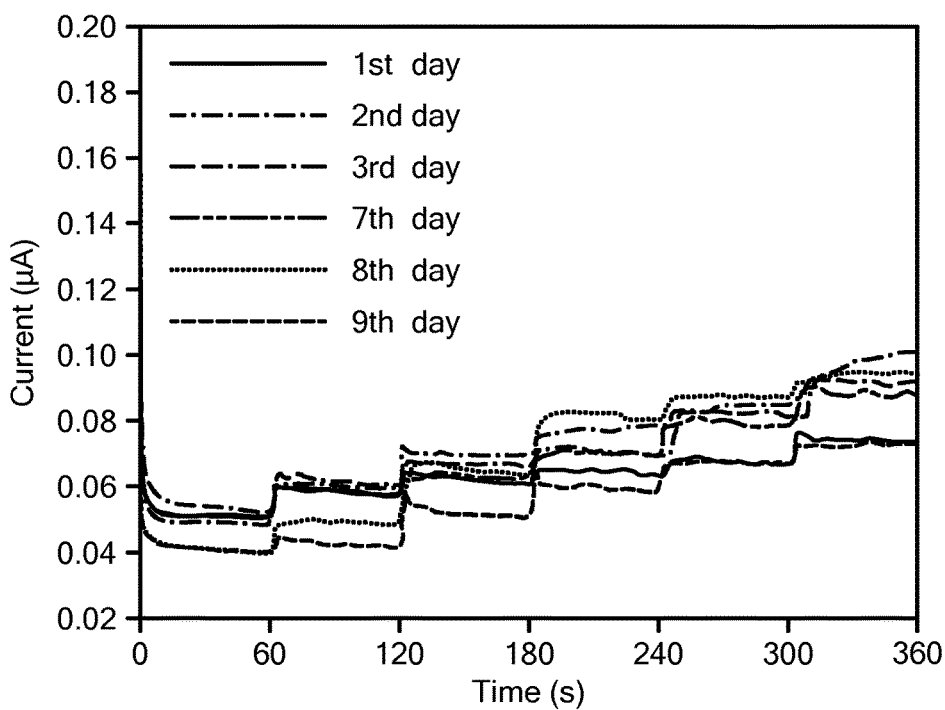
FIG. 12D illustrates the time course of L-lactate detection for the data shown in FIG. 12C.
Figure 12E:
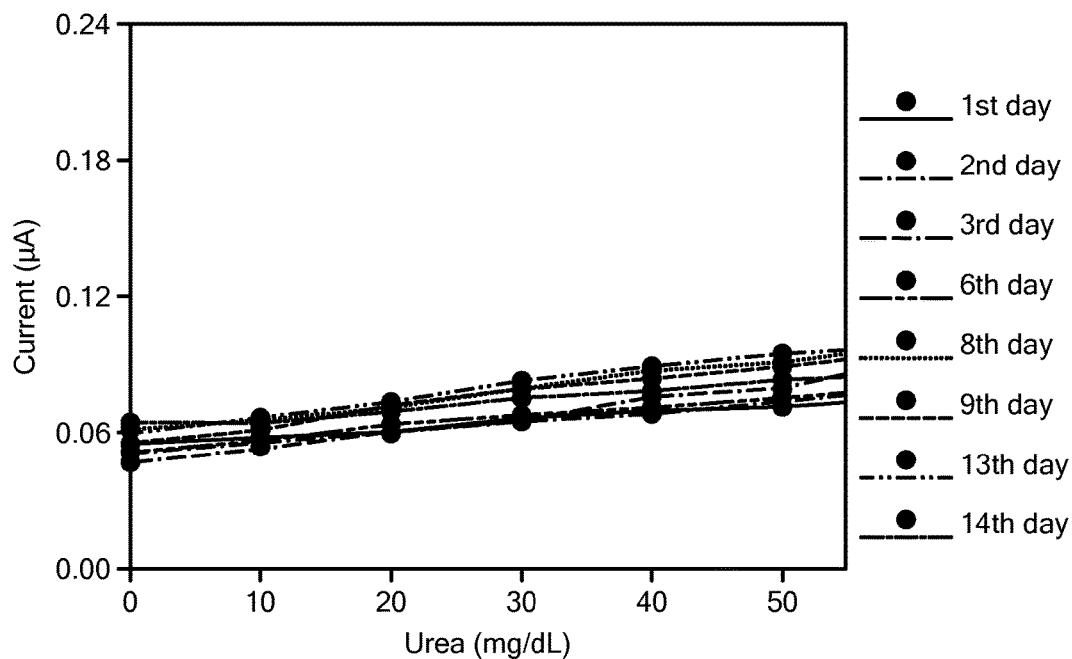
FIG. 12E illustrates the stability of the urease-functionalized SWNT biosensor for urea detection.
Figure 12F:
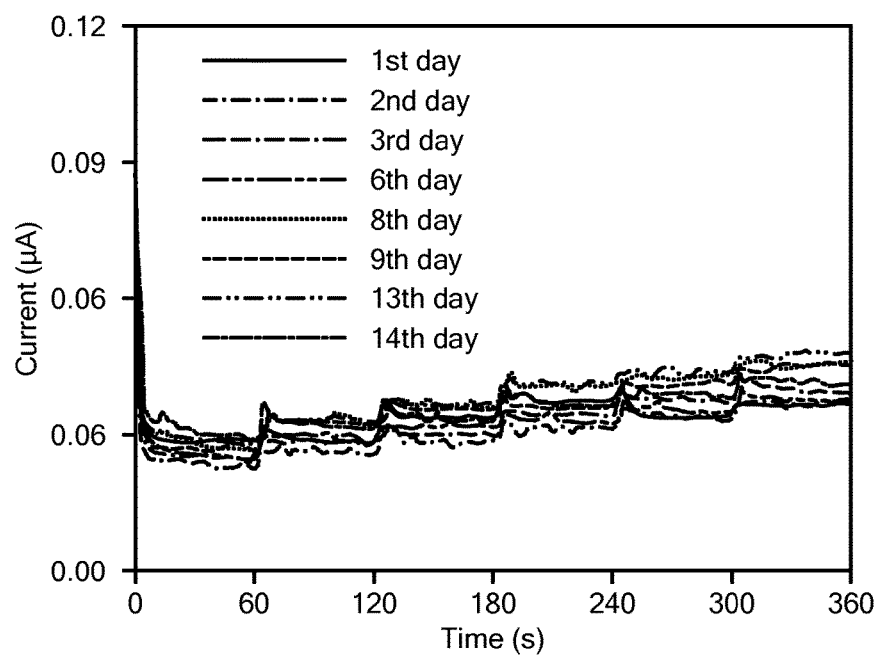
FIG. 12F illustrates the time course of urea detection for the data shown in FIG. 12E.

Resistance response was measured to identify the assembly of SWNTs, linker (PBSE), and enzyme (GOD) onto a template, compared with those of semiconducting-metallic mixed SWNTs assembly (FIG. 10A). The more assembled materials led to increased resistance response. G-L-C (GOD-linker-SWNT) assembly of both mixed and semiconducting SWNTs (0.43 and 0.6 kohm, respectively) obtained the highest resistance results. In addition, the resistance response of semiconducting SWNTs (FIG. 10B) was higher than that of metallic/semiconducting mixed SWNT assembly. When immobilized enzyme was added onto an SWNT bundle, the width of the SWNTs was increased and the space between SWNTs became narrowed (compare FIGS. 6A and 6B). When the SWNT bundle was modified with linker and enzyme (GOD), the $R/R_o$ ratio of resistance responses were increased to ca. 1.3 and ca. 1.7, respectively. The more sensitive electrical properties of semiconducting SWNTs were preferred in the biosensor compared to the weaker responses of mixed SWNTs.

Example 4

Increased Biosensor Resistance in Response to Glucose

Figure 8A:
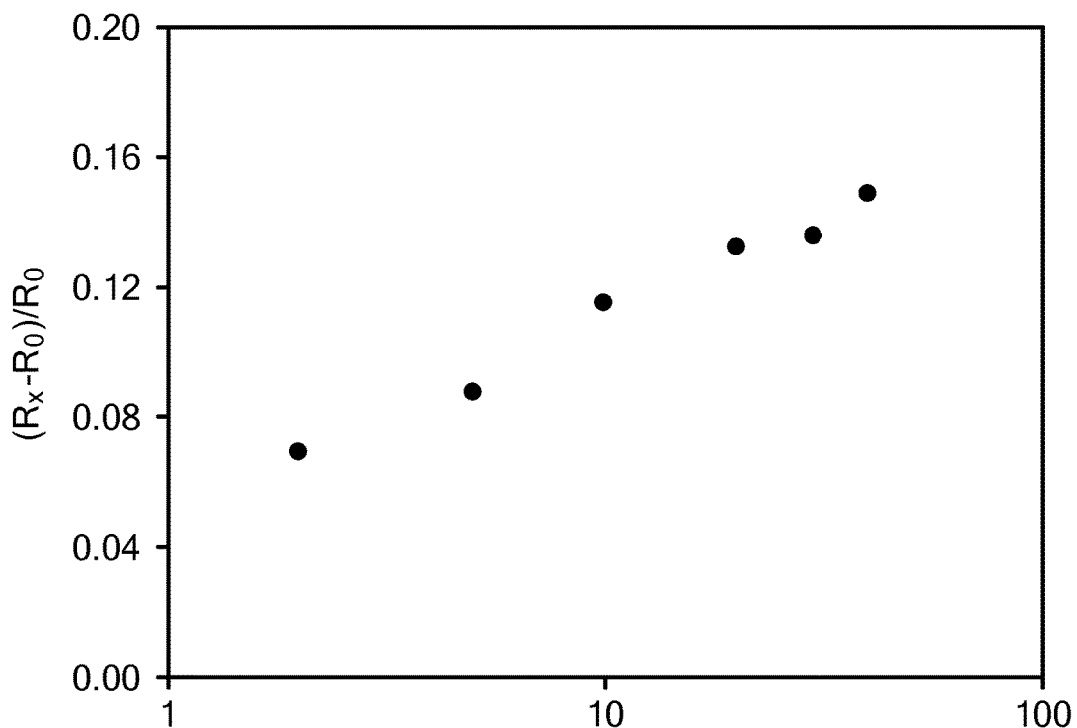
FIG. 8A shows the linearity of resistance response of the glucose-oxidase-functionalized biosensor to glucose in the mM concentration range.
Figure 8B:
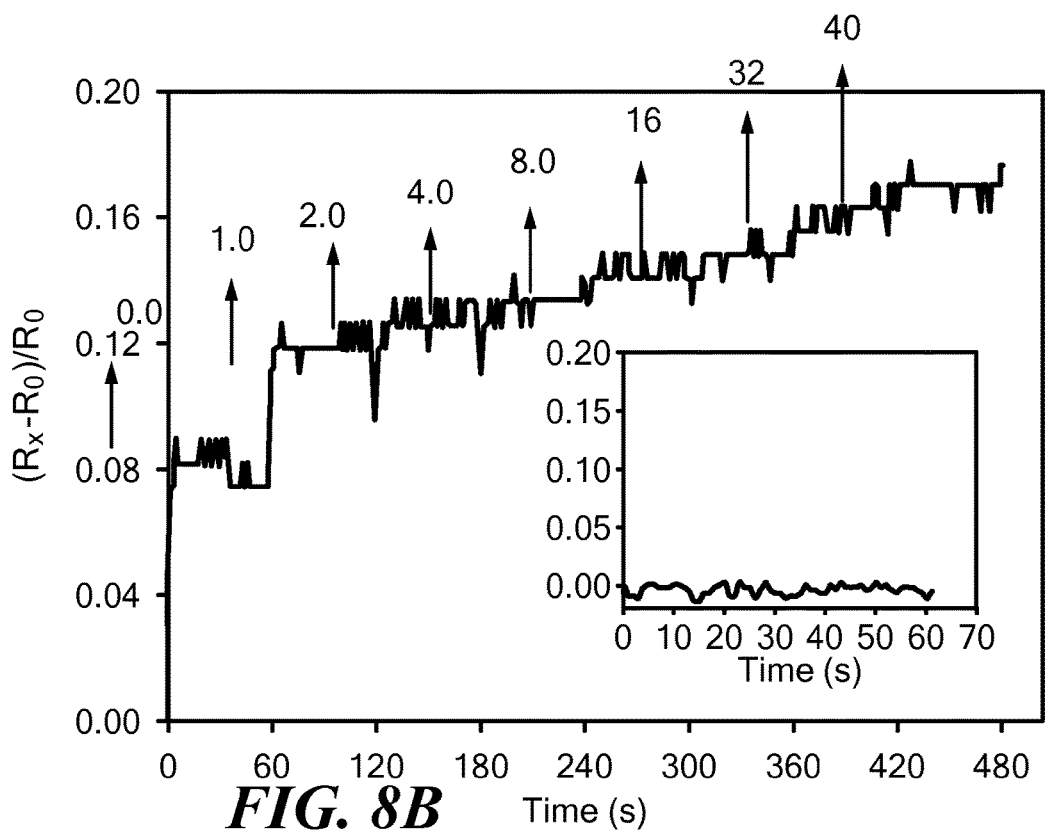
FIG. 8B shows the time course of resistance responses of the biosensor to glucose.

Linear dependence of resistance responses of a GOD-modified SWNT biosensor device on glucose concentration were obtained (FIG. 8A). The biosensor exhibited a rapid and sensitive response to D-glucose up to 50 mM, while there was no amperometric response of a device containing a non-GOD-immobilized SWNT bundle at over 20.0 mM of D-glucose. The time course of resistance response of the biosensor in dependence on D-glucose concentration was also performed at ambient condition (PBS pH 7.4 and 25° C.), The results are shown in FIG. 8B. The time course of resistance responses was sensitive to D-glucose concentration. The response time was sufficient for sensing diabetic glucose levels if the measurement time is conducted for as little as 500 s. The results showed that the biosensor was able to detect D-glucose at least in the range of 0-40 mM.

Figure 9A:
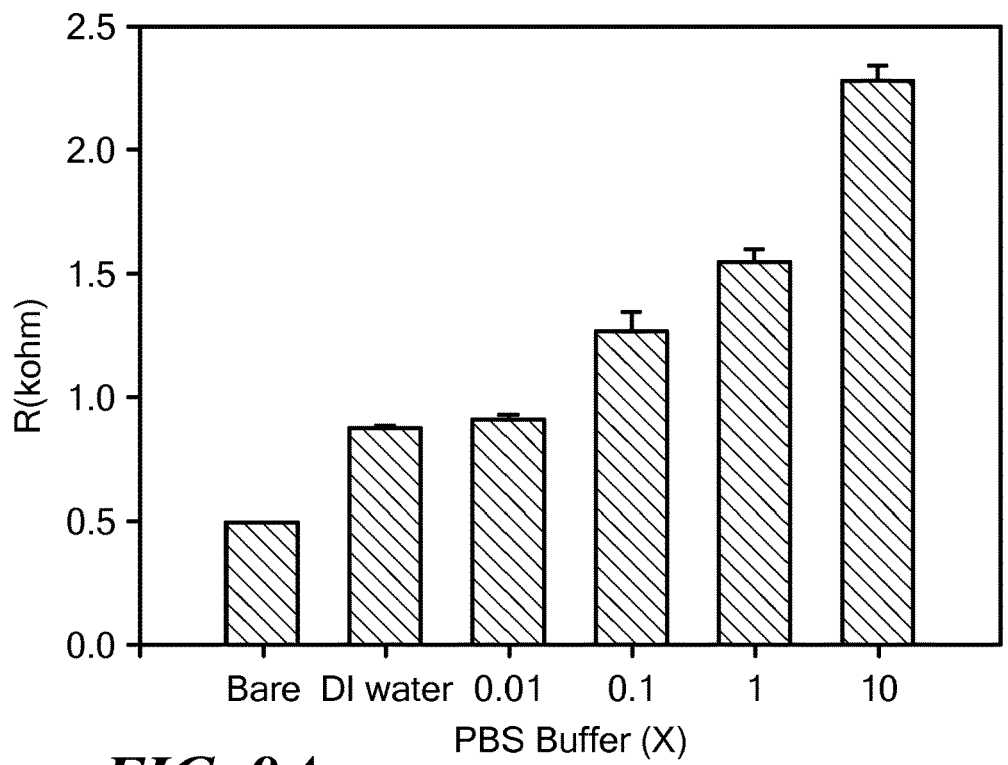
FIG. 9A shows the effect of PBS buffer concentration on resistance of the glucose oxidase-functionalized SWNT biosensor.
Figure 9B:
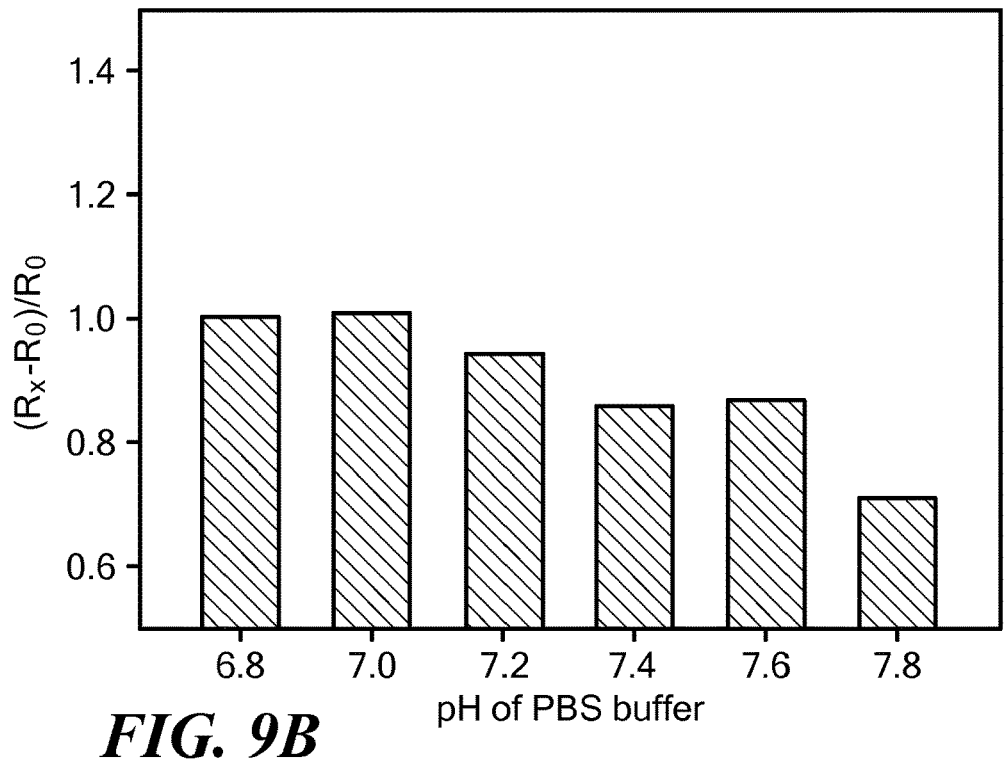
FIG. 9B shows the effect of the pH of PBS buffer on resistance of the glucose oxidase-functionalized SWNT biosensor.

The effects of buffer concentration and pH on resistance are shown in FIGS. 9A-9B. Higher concentration of PBS buffer gave higher resistances while resistance response of only DI water (about 0.8) was a litter lower than that of 0.01 M PBS. Though buffer solution with high concentration provided high ionic strength, it was not affected by electron transfer through the SWNT bundle with the immobilized GOD. In addition, lower pH values of PBS buffer yielded higher resistances, while over the pH region of PBS buffer from 6.8-7.8 (similar to the physiological condition in blood), the resistance response of GOD-modified SWNTs began to decrease from neutral pH (7.0) upward. It was expected that $H_3O^+$ ion is more effective at the increasing resistance response than $OH^-$ ion in PBS buffer.

Example 5

Repeatability, Stability, and Sensitivity of Biosensor for D-Glucose, L-Lactate, and Urea Detection The repeatability, stability, and sensitivity of the developed biosensor for D-glucose, L-lactate, and urea detection are illustrated in FIGS. 11A-11F. These figures show the repeatability of D-glucose, L-lactate, and urea detection using an enzyme-modified semiconductor SWNT biosensor. The various concentrations of glucose (0, 4.0, 8.0, 12, 16, and 20 mM), L-lactate (0, 1.0, 2.0, 3.0, 4.0, and 5.0 g/L), and urea (0, 10, 20, 30, 40, 50 mg/dL) every 60 sec 5.0 g/L of concentrated substrate were injected into the working solution for real time detection of D-glucose, L-lactate, and urea with 1.0 mV. The detection using the enzyme-modified SWNT biosensor of the invention responded with a similar current for 10 or 9 duplicates times at each biomolecule's concentrations while the real time detection of each target biomolecule obtained essentially the same current response for each concentration, considering the errors of experimental handling. In addition, FIGS. 12A-12F show the stability of the enzyme-modified SWNT biosensor for physiological detection of D-glucose, L-lactate, and urea.

The electrical responses maintained a similar slope of concentration dependence for D-glucose, L-lactate, and urea over a week. Real time detection for stability were performed as the followed repeatability test with various concentrations. In real time D-glucose and urea detections were stable over about 2 weeks even though the current responses were a little changed during the second week, while L-lactate detection was stable for 9 days. The currents continuously increased as a function of concentration in time of detection assays of D-glucose, L-lactate, and urea, though the current range dependence on urea concentration was smaller than that for the other substrates.

Figure 13A:
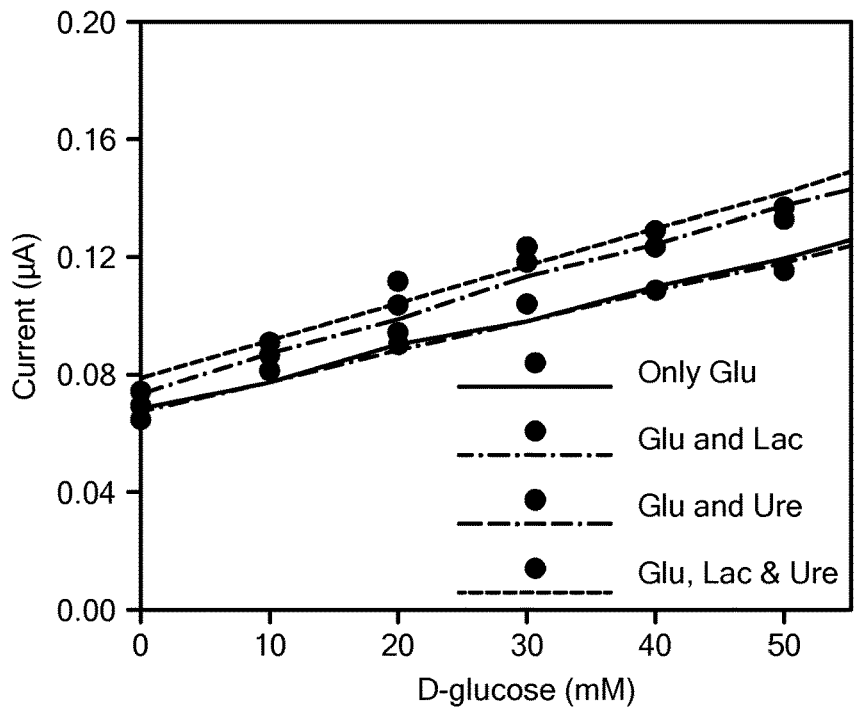
FIG. 13A illustrates the effect of the presence of L-lactate or urea on the detection of D-glucose using a multiplex biosensor.
Figure 13B:
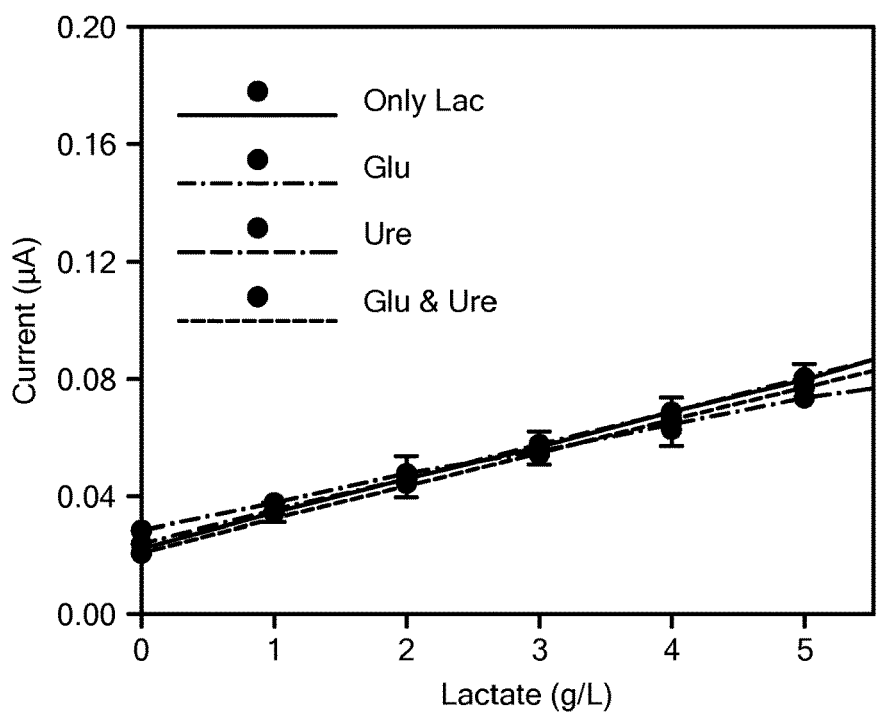
FIG. 13B illustrates the effect of the presence of D-glucose or urea on the detection of L-lactate using the multiplex biosensor.
Figure 13C:
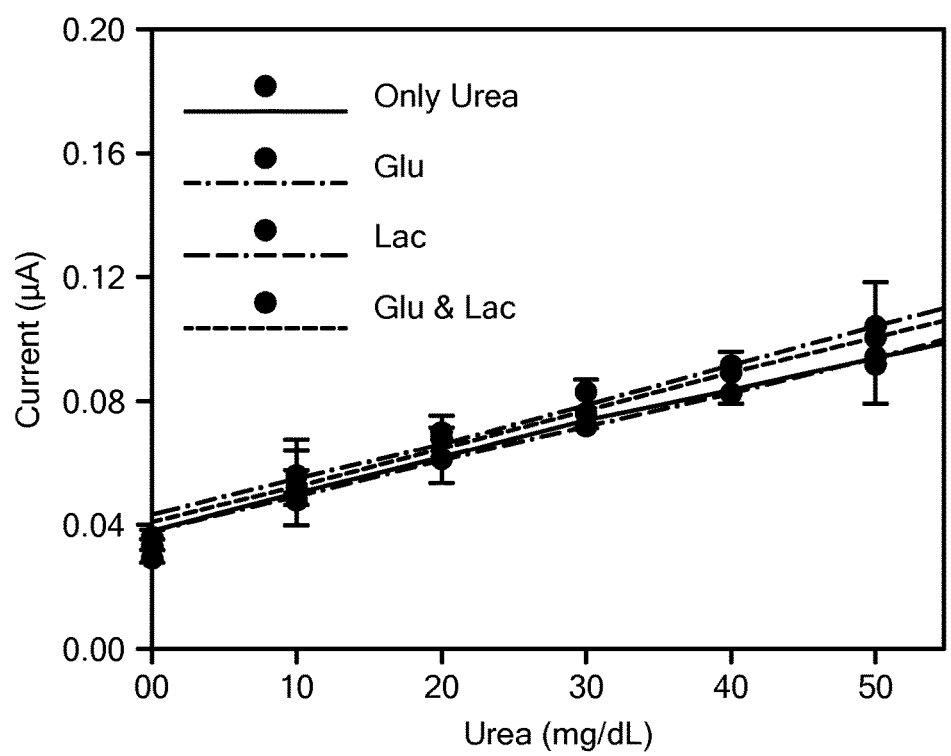
FIG. 13C illustrates the effect of the presence of D-glucose or L-lactate on the detection of urea using the multiplex biosensor.

The effect of other biomolecules on detection of a different target is illustrated in FIGS. 13A-13C. The various concentrations of glucose (0, 10, 20, 30, 40, and 50 mM), L-lactate (0, 1.0, 2.0, 3.0, 4.0, and 5.0 g/L), and urea (0, 10, 20, 30, 40, 50 mg/dL) with each 5.0 µl of sample loading were utilized for detection.

There was little effect of other biomolecules on the detection of L-lactate or urea using the developed SWNTs sensor, though the presence of urea slightly affected D-glucose detection in that the current response was increased.

Figure 14A:
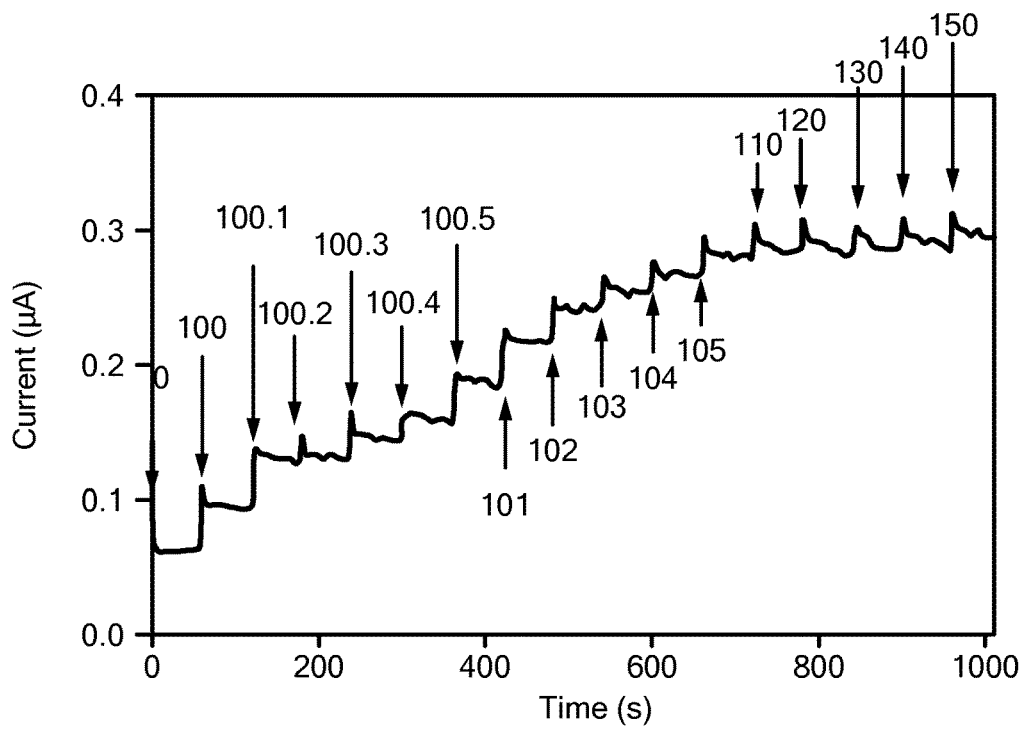
FIG. 14A illustrates the sensitivity of a multiplex biosensor to D-glucose over a wide range of concentrations (0, 100, 100.1, 100.2, 100.3, 100.4, 100.5, 101, 102, 103, 104, 105, 110, 120, 130, 140, and 150 mg/dl).
Figure 14B:
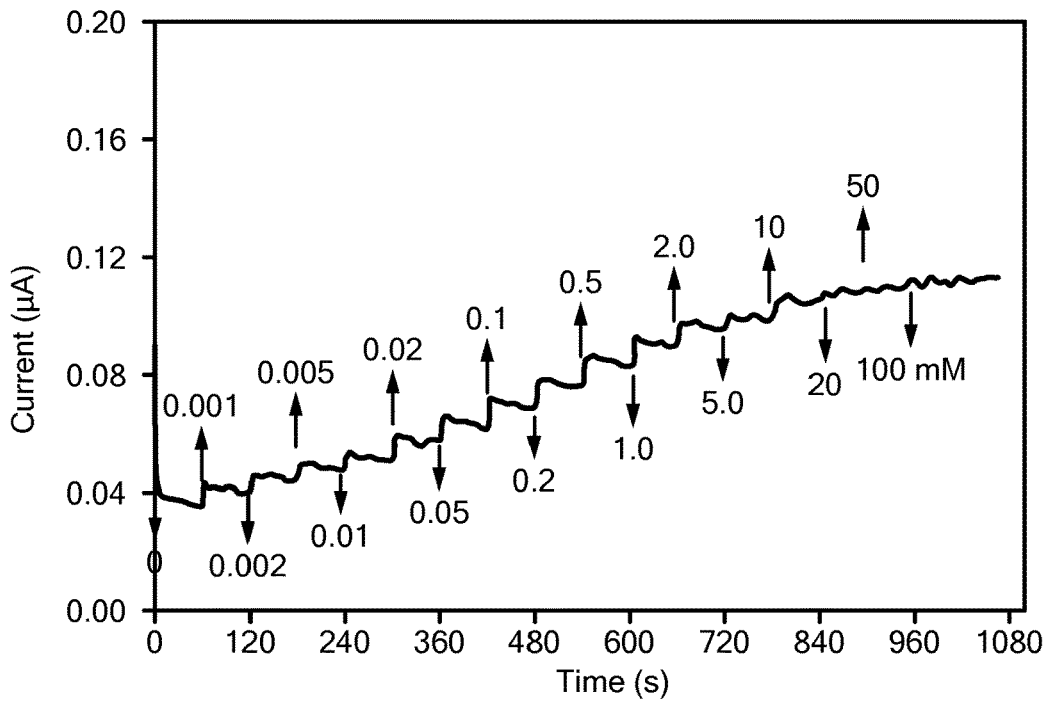
FIG. 14B illustrates the sensitivity of the multiplex biosensor to L-lactate over a wide range of concentrations (0, 0.001, 0.002, 0.005, 0.01, 0.02, 0.05, 0.1, 0.2, 0.5, 1.0, 2.0, 5.0, 10, 20, 50, 100 mM).
Figure 14C:
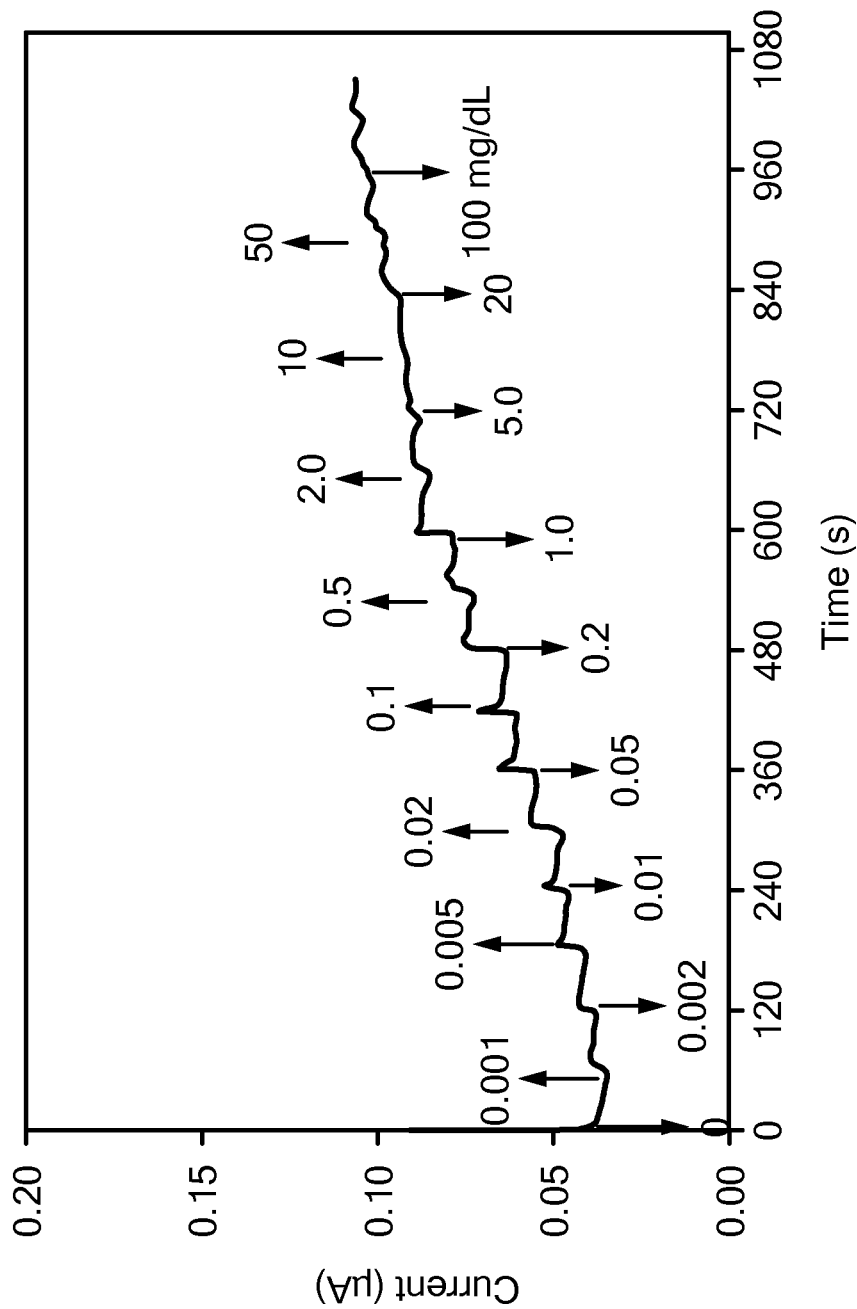
FIG. 14C illustrates the sensitivity of the multiplex biosensor to urea over a wide range of concentrations (0, 0.001, 0.002, 0.005, 0.01, 0.02, 0.05, 0.1, 0.2, 0.5, 1.0, 2.0, 5.0, 10, 20, 50, 100 mg/dL).

In summary, the biosensor using semiconductor SWNTs was able to detect D-glucose, L-lactate, and urea at the same time. The detection sensitivities of D-glucose, L-lactate, and urea using the enzyme-modified semiconductor SWNT biosensor were shown to span a large range of concentrations. (FIGS. 14A-14C) The various concentrations of glucose (0, 100, 100.1, 100.2, 100.3, 100.4, 100.5, 101, 102, 103, 104, 105, 110, 120, 130, 140, and 150 mg/dl), L-lactate (0, 0.001~0.005, 0.01~0.05, 0.1~0.5, 1.0~5.0, and 10~100 mM), and urea (0, 0.001~0.005, 0.01~0.05, 0.1~0.5, 1.0~5.0, and 10~100 mg/dL) with 5.0 µl of loading every 60 sec were injected into the working solution for real time detections with 1.0 mV. The increasing current responses following various concentrations of three biomolecules were dramatically observed in real time detection for about 1000 sec. The enzyme-modified semiconductor SWNT biosensors were sensitive over 0~150 mg/dl, 0~100 mM, and 0~100 mg/dL for detection ranges and 0.1 mg/dl, 0.001 mM, and 0.001 mg/dL for detection limits of D-glucose, L-lactate, and urea, respectively. it was noted that small current responses were obtained within the high range of each concentration due to the added quantity at each level.

REFERENCES

1. Cella, L. N., Chen, W., Myung, N. V., Mulchandani, A.: Single-Walled Carbon Nanotube-Based Chemiresistive Affinity Biosensors for Small Molecules: Ultrasensitive Glucose Detection, J. Am. Chern. Soc., 132, 5024-5026 (2010).
2. Avouris, P. and Chen, J.: Nanotube electronics and optoelectronics, Mater. Today, 9, 46-54 (2006).
3. Dai, H.: Carbon Nanotubes:D Synthesis, Integration, and Properties, Ace. Chern. Res., 35, 1035-1044 (2002).
4. Merkoci, A., Pumera, M., Llopis, X., Perez, B., Valle, M. D., Alegret S.: New materials for electrochemical sensing VI: Carbon nanotubes, Trends Anal. Chern., 24, 826-838 (2005).
5. Schasfoort, R. B. M., Bergveld, P., Kooyman, R. P. H., Greve J.: Possibilities and limitations of direct detection of protein charges by means of an immunological field-effect transistor, Anal. Chim. Acta., 238, 323-329 (1990).
6. Schasfoort, R. B. M., Kooyman, R. P. H., Bergveld, P., Greve, J.: A new approach to immunoFET operation, Biosens. Bioelectron., 5, 103-124 (1990).
7. Khan, F., He, M., Taussig, M. J.: Double-hexahistidine tag with high-affinity binding for protein immobilization, purification, and detection on Ni-nitrilotriacetic acid surfaces, Anal. Chern., 78. 3072-3079 (2006).
8. Kusnezow, W., Hoheisel, J. D. J.: Solid supports for microarray immunoassays, Mol. Recognit. 16, 165-176 (2003).
9. Katz, E., Willner, I., Kotlyar, A. B.: A non-compartmentalized glucose-02 biofuel cell by bioengineered electrode surfaces, J. Electroanal. Chern., 479, 64-68 (1999).
10. Lee, J. Y., Shin, H. Y., Lee, J. H., Song, Y. S., Kang, S. W., Park, C., Kim, J. B., Kim, S. W.: A novel enzyme-immobilization method for a biofuel cell, J. Mol. Catal. B: Enzym., 59, 274-278 (2009).

11. Ramanavicius, A., Kausaite, A., Ramanaviciene, A.: Biofuel cell based on direct bioelectrocatalysis, Biosens. Bioelectron., 20, 1962-1967 (2005).
12. Jaber-Ansari, L., Hahm, M. G., Kim, T. H., Somu, S., Busnaina, A., Jung, Y. J.: Large scale highly organized single-walled carbon nanotube networks for electrical devices, Appl. Phys. A., 96, 373-377 (2009).
13. Kim, Y. L., Li, B., An, X., Hahm, M. G., Chen, L., Washington, M., Ajayan, P. M., Nayak, S. K., Busnaina, A., Kar, S., Jung, Y. J.: Highly Aligned Scalable Platinum-Decorated Single-Wall Carbon Nanotube Arrays for Nanoscale Electrical Interconnects, ACS Nano., 3, 2818-2826 (2009).
14. Jaber-Ansari, L., Hahm, M. G., Somu, S., Sanz, Y. E., Busnaina, A., Jung, Y. J.: Mechanism of Very Large Scale Assembly of SWNTs in Template Guided Fluidic Assembly Process, J. Am. Chern. Soc., 131, 804-808 (2009).
15. Yang, M., Bruck, H. A., Kostov, Y., Rasooly, A.: Biological semiconductor based on electrical percolation, Anal. Chern., 82, 3567-3572 (2010).
16. Feng, C. L., Xu, Y. H., Song, L. M.: Study on highly sensitive potentiometric IgG immunosensor, Sens. Actuators B, 66, 190-192 (2000).
17. Kamahori, M, Ishige Y., Shimada, M.: A novel enzyme immunoassay based on potentiometric measurement of molecular adsorption events by an extended-gate field-effect transistor sensor, Biosens. Bioelectron., 22, 3080-3085 (2007).

The invention claimed is:

1. A microscale multiplex biosensor configured for real time, simultaneous detection of two or more different chemical agents selected from the group consisting of D-glucose, L-lactate, and urea, the biosensor comprising:
   a substrate;
   a conductive layer attached to a surface of the substrate, the conductive layer forming at least first and second pairs of electrodes with an insulating gap between the electrodes of each pair; and
   a first conductive bridge between the first pair of electrodes and a second conductive bridge between the second pair of electrodes, each conductive bridge consisting essentially of one or more functionalized single-walled carbon nanotubes contacting the pair of electrodes and bridging the gap between the pair of electrodes;
   wherein the one or more nanotubes of the first conductive bridge are functionalized via a linker with a first enzyme that reacts with a first chemical agent selected from the group consisting of D-glucose, L-lactate, and urea, whereby the conductivity of the first conductive bridge is modified;
   wherein the one or more nanotubes of the second conductive bridge are functionalized via a linker with a second enzyme that reacts with a second chemical agent selected from the group consisting of D-glucose, L-lactate, and urea, wherein the second chemical agent is different from the first chemical agent, whereby the conductivity of the second conductive bridge is modified; and
   wherein the linker is 1-pyrenebutanoic acid succinimidyl ester.

2. The biosensor of claim 1, wherein the single-walled carbon nanotubes are semiconducting.

3. The biosensor of claim 1, further comprising a circuit for receiving and/or processing of an electrical signal from said electrodes.

4. The biosensor of claim 1, wherein the circuit comprises an amperometry circuit.

5. The biosensor of claim 1, further comprising a transmitter for sending data obtained by the biosensor to a remote receiver.

6. The biosensor of claim 1, further comprising a third pair of electrodes and a gap between the electrodes and a third conductive bridge consisting essentially of one or more functionalized single-walled carbon nanotubes, each bridging a gap between the third pair of electrodes;
   wherein the one or more nanotubes of the third conductive bridge are functionalized via a 1-pyrenebutanoic acid succinimidyl ester linker with a third enzyme that reacts with a third chemical agent selected from the group consisting of D-glucose, L-lactate, and urea, wherein the third chemical agent is different from the first and second chemical agents, whereby the conductivity of the second conductive bridge is modified.

7. The biosensor of claim 1 that is configured for implantation within a subject and providing continuous or periodic detection of said chemical agent.

8. The biosensor of claim 1 that is configured for accepting a body fluid sample of a subject.

9. The biosensor of claim 8 further comprising one or more microfluidic pathways for presenting said body fluid sample to said functionalized conductive bridge.

10. The biosensor of claim 1 that provides quantification of a level of said chemical agent.

11. The biosensor of claim 1, wherein reaction of said first chemical agent with said first enzyme results in increased electrical resistance of said first conductive bridge, and wherein reaction of said second chemical agent with said second enzyme results in increased resistance of said second conductive bridge.

* * * * *